(12) United States Patent
Abe et al.

(10) Patent No.: US 9,186,125 B2
(45) Date of Patent: Nov. 17, 2015

(54) ULTRASONIC DIAGNOSTIC APPARATUS FOR GENERATING THREE DIMENSIONAL CARDIAC MOTION IMAGE BY SETTING LINE SEGMENTED STRAIN GAUGES

(75) Inventors: Yasuhiko Abe, Otawara (JP); Tetsuya Kawagishi, Nasushiobara (JP)

(73) Assignees: KABUSHIKI KAISHA TOSHIBA, Tokyo (JP); Toshiba Medical Systems Corporation, Otawara-shi (JP)

(*) Notice: Subject to any disclaimer, the term of this patent is extended or adjusted under 35 U.S.C. 154(b) by 692 days.

(21) Appl. No.: 12/487,399

(22) Filed: Jun. 18, 2009

(65) Prior Publication Data
US 2009/0318803 A1 Dec. 24, 2009

(30) Foreign Application Priority Data
Jun. 19, 2008 (JP) ................................ 2008-160744

(51) Int. Cl.
*A61B 8/00* (2006.01)
*A61B 8/08* (2006.01)
*A61B 6/00* (2006.01)

(52) U.S. Cl.
CPC .............. *A61B 8/08* (2013.01); *A61B 8/0883* (2013.01); *A61B 6/503* (2013.01)

(58) Field of Classification Search
CPC ......... A61B 8/0883; A61B 6/503; A61B 8/08
USPC .................. 345/419, 428; 382/128, 130, 131; 600/437, 438, 441, 443, 447, 450, 454, 600/458, 508
See application file for complete search history.

(56) References Cited

U.S. PATENT DOCUMENTS

| 6,447,453 | B1 | 9/2002 | Roundhill et al. | |
|---|---|---|---|---|
| 6,494,834 | B2 * | 12/2002 | Konofagou et al. | 600/438 |
| 6,508,768 | B1 * | 1/2003 | Hall et al. | 600/443 |
| 6,638,225 | B2 * | 10/2003 | Kamiyama | 600/443 |

(Continued)

FOREIGN PATENT DOCUMENTS

| JP | 11-155862 A | 6/1999 |
|---|---|---|
| JP | 2003-79627 A | 3/2003 |

(Continued)

OTHER PUBLICATIONS

3D Echocardiography: A Review of the Current Status and Future Directions Judy Hung, MD, Roberto Lang, MD, Frank Flachskampf, MD, Stanton K. Shernan, MD, Marti L. McCulloch, RDCS, David B. Adams, RDCS, James Thomas, MD, Mani Vannan, MD, and Thomas Ryan, MD, Boston, Massachusetts; Chicago, Illinois; Erlangen, Germany; Galveston, Texas; Durham, North.*

(Continued)

*Primary Examiner* — Unsu Jung
*Assistant Examiner* — Serkan Akar
(74) *Attorney, Agent, or Firm* — Oblon, McClelland, Maier & Neustadt, L.L.P.

(57) ABSTRACT

A plurality of strain gauges defined by gauge endpoints are set in each time phase using motion vector information of tissue, and a three-dimensional strain gauge image in which each strain gauge is disposed at a three-dimensional position corresponding to, for example, an ultrasonic image in each time phase is generated and displayed. Moreover, an MPR image is set on volume data and is displayed in a predetermined form in a state where gauge coordinates are projected thereon.

36 Claims, 16 Drawing Sheets

(56) References Cited

U.S. PATENT DOCUMENTS

| | | | | |
|---|---|---|---|---|
| 6,951,543 | B2* | 10/2005 | Roundhill | 600/443 |
| 7,175,598 | B2* | 2/2007 | Yoneyama | 600/443 |
| 7,327,862 | B2* | 2/2008 | Murphy et al. | 382/128 |
| 2002/0072672 | A1* | 6/2002 | Roundhill et al. | 600/450 |
| 2002/0072674 | A1* | 6/2002 | Criton et al. | 600/454 |
| 2003/0083578 | A1* | 5/2003 | Abe et al. | 600/447 |
| 2004/0267124 | A1* | 12/2004 | Roundhill | 600/443 |
| 2005/0085729 | A1* | 4/2005 | Abe | 600/450 |
| 2005/0101863 | A1* | 5/2005 | Kawagishi et al. | 600/443 |
| 2006/0036172 | A1* | 2/2006 | Abe | 600/443 |
| 2006/0074315 | A1 | 4/2006 | Liang et al. | |
| 2006/0084874 | A1* | 4/2006 | Imamura et al. | 600/447 |
| 2006/0098853 | A1* | 5/2006 | Roundhill et al. | 382/128 |
| 2006/0116583 | A1* | 6/2006 | Ogasawara et al. | 600/458 |
| 2006/0122512 | A1* | 6/2006 | Abe | 600/454 |
| 2006/0241447 | A1* | 10/2006 | Harada et al. | 600/443 |
| 2007/0038087 | A1* | 2/2007 | Abe et al. | 600/437 |
| 2007/0071295 | A1* | 3/2007 | Jackson | 382/128 |
| 2007/0118041 | A1* | 5/2007 | Nishiura et al. | 600/508 |
| 2008/0009722 | A1* | 1/2008 | Simopoulos et al. | 600/437 |
| 2008/0019580 | A1* | 1/2008 | Ohyu et al. | 382/130 |
| 2008/0051661 | A1* | 2/2008 | Kataguchi et al. | 600/455 |
| 2008/0077013 | A1* | 3/2008 | Kawagishi et al. | 600/443 |
| 2008/0089571 | A1* | 4/2008 | Kurita | 382/131 |
| 2008/0267482 | A1 | 10/2008 | Abe et al. | |
| 2009/0069680 | A1 | 3/2009 | Abe | |

FOREIGN PATENT DOCUMENTS

| | | |
|---|---|---|
| JP | 2003-175041 | 6/2003 |
| JP | 2003-250804 A | 9/2003 |
| JP | 2005-253636 A | 9/2005 |
| JP | 2006-75590 A | 3/2006 |
| JP | 2006-141509 A | 6/2006 |
| JP | 2007-44499 A | 2/2007 |
| JP | 2007-117252 A | 5/2007 |
| JP | 2007-117611 | 5/2007 |
| JP | 2007-130063 A | 5/2007 |
| JP | 2007-143606 A | 6/2007 |
| JP | 2007-236606 A | 9/2007 |
| JP | 2007-319190 A | 12/2007 |
| WO | WO 2007/046074 A1 | 4/2007 |
| WO | WO 2008/026022 A1 | 3/2008 |

OTHER PUBLICATIONS

Yamamoto, Tomoko Machino, Ryo Kawamura and Kazutaka Aonuma Yoshihiro Seo, Tomoko Ishizu, Yoshiharu Enomoto, Haruhiko Sugimori, Masayoshi Myocardial Deformation Validation of 3-Dimensional Speckle Tracking Imaging to Quantify Regional Circ Cardiovasc Imaging 2009;2;451-459; originally published online Sep. 12, 2009.*

An Elen, Hon Fai Choi, Dirk Loeckx, Member, IEEE, Hang Gao, Piet Claus, Paul Suetens, Member, IEEE, Frederik Maes, and Jan D'hooge, Member, IEEE Three-Dimensional Cardiac Strain Estimation Using Spatio-Temporal Elastic Registration of Ultrasound Images: A Feasibility Study, IEEE Transactions on Medical Imaging, vol. 27, No. 11, Nov. 2008.*

Victor Mor-Avi, Lissa Sugeng and Roberto M. Lang , Routine Echocardiographic Examination in Adult Patients? Real-Time 3-Dimensional Echocardiography: An Integral Component of the Circulation is published by the American Heart Association. 7272 Greenville Avenue, Dallas, TX DOI: 10.1161/CIRCULATIONAHA. 107.751354 Circulation 2009;119;314-329.*

Clinical Investigations Ventricular Function Three-Dimensional-Wall Motion Tracking: A New and Faster Tool for Myocardial Strain Assessment:Comparison With Two-Dimensional-Wall Motion Tracking Leopoldo Pe'rez de Isla, MD, David Vivas Balcones, MD, Covadonga Ferna'ndez-Golfi'n, MD, Pedro Marcos-Alberca, MD, Carlos Almeri'a, MD, Jose' Luis Rodrigo.*

Three Dimensional Segmentation of the Heart Muscle in Real-Time 3D Echocardiographic Sequences Using Image Statistics MM Nillesenl, RGP Lopatal, IH Gerrits1, L Kapusta2,HJ Huisman3, JM Thijssen1, CL de Korte1 1Clinical Physics Laboratory, Department of Pediatrics, 2Children's Heart Centre, Computers in Cardiology 2006;33:129-132.*

Ogawa et al, Usefulness of Automated Quantitation of Regional Left Ventricular Wall Motion by a Novel Method of Two-Dimensional Echocardiographic Tracking, doi:10.1016/j.amjcard.2006.06.060.*

English Translation of JP-2007-117252, May 2007.*

English Translation of JP-2007-143606, Jun. 2007.*

English Translation of JP-2007-044499, Feb. 2007.*

U.S. Appl. No. 12/540,135, filed Aug. 12, 2009, Ohuchi, et al.

Keitaro Ogawa, et al. "Usefulness of Automated Quantitation of Regional Left Ventricular Wall Motion by a Novel Method of Two-Dimensional Echocardiographic Tracking", Quantitation of Wall Motion by 2D Tracking, Manuscript, Department of Internal Medicine and Cardiology, Osaka City University Medical School, Osaka, Japan, 2006, 23 pages.

Office Action issued Jan. 8, 2013 in Japanese Patent Application No. 2008-160744 (with English-language translation).

Office Action issued Apr. 22, 2014 in Japanese Patent Application No. 2013-048462 (with English language translation).

* cited by examiner

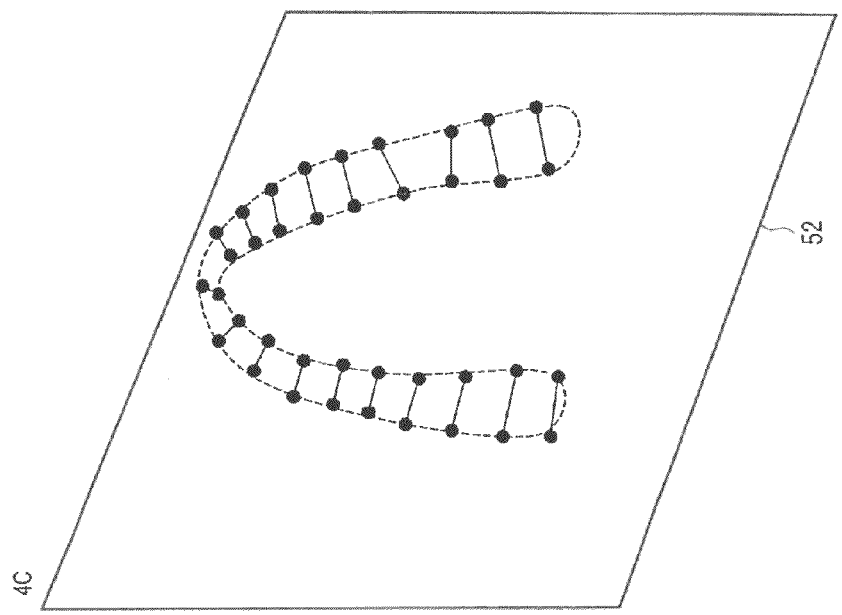
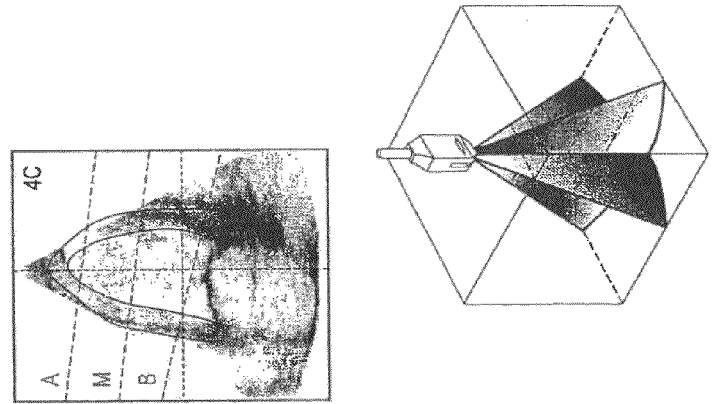
FIG. 6

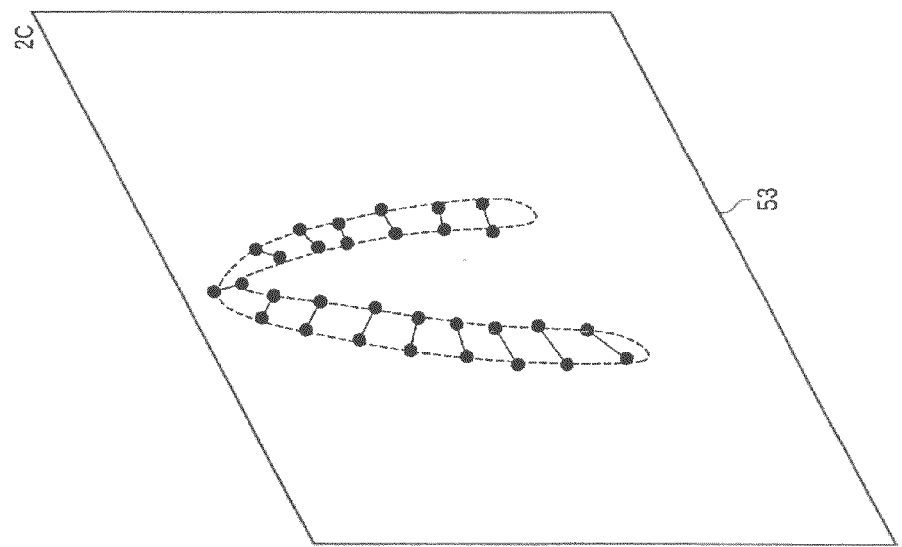
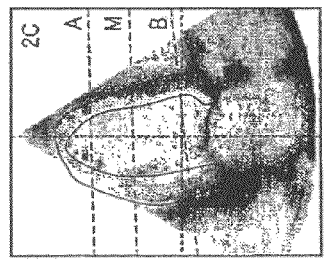
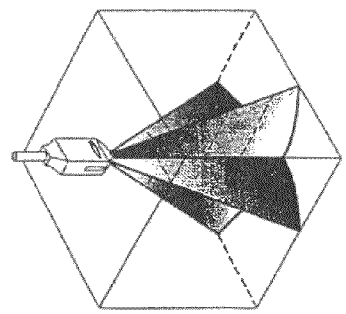
FIG. 7

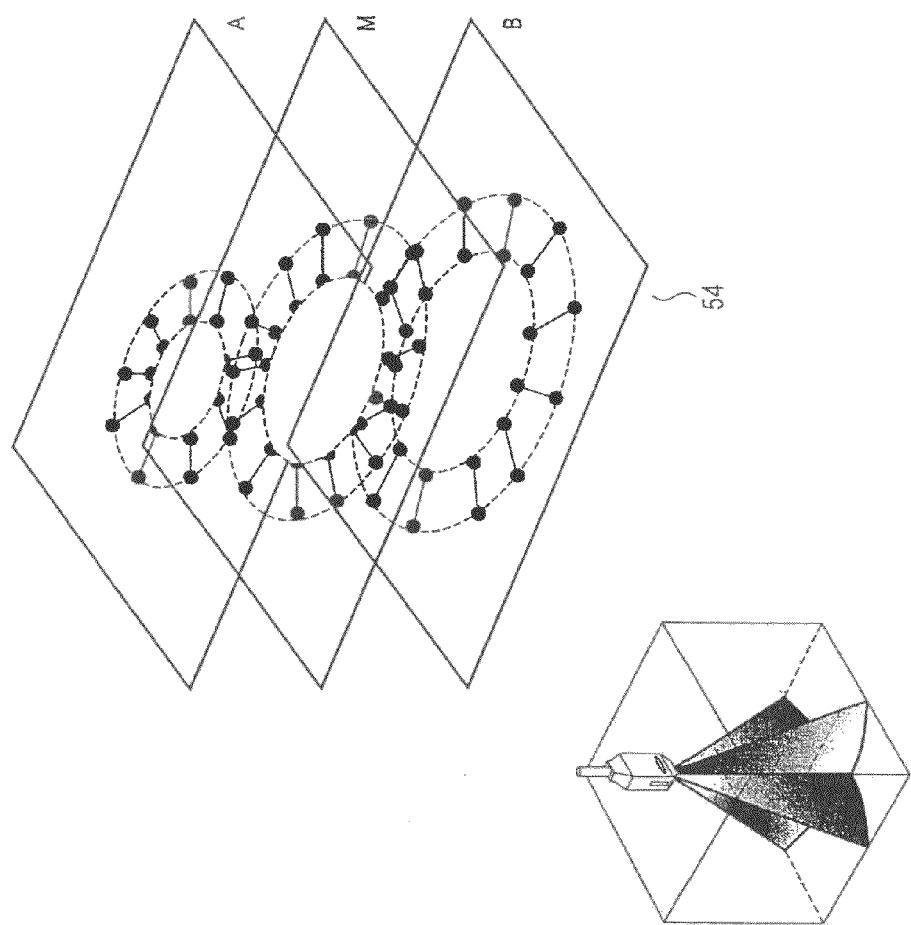
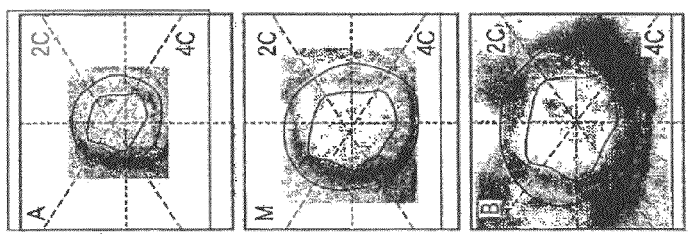
FIG. 8

ULTRASONIC DIAGNOSTIC APPARATUS FOR GENERATING THREE DIMENSIONAL CARDIAC MOTION IMAGE BY SETTING LINE SEGMENTED STRAIN GAUGES

CROSS-REFERENCE TO RELATED APPLICATIONS

This application is based upon and claims the benefit of priority from prior Japanese Patent Application No. 2008-160744, filed Jun. 19, 2008, the entire contents of which are incorporated herein by reference.

BACKGROUND OF THE INVENTION

1. Field of the Invention

The present invention relates to an ultrasonic diagnostic apparatus, an ultrasonic image processing apparatus, and a medical image processing apparatus for supporting intuitive recognition of complicated wall motion resulting from a multi-layered structure of a myocardium by displaying a gauge divided between endomyocardial and epimyocardial layers of the heart, for example, so as to overlap on a medical image, such as an ultrasonic image, when evaluating the movement of tissue using an ultrasonic image.

2. Description of the Related Art

For body tissue, such as a myocardium, it is very important for diagnosis of the tissue to evaluate the function objectively and quantitatively. In recent years, various quantitative evaluation methods have been tried mainly for the heart as an example.

For example, as disclosed in JP-A-2003-175041, a technique called speckle tracking for calculating wall motion information on a local portion, such as displacement or strain, while tracking a local region of an image acquired by an ultrasonic diagnostic apparatus, for example, has already been put to practical use. Moreover, as disclosed in JP-A-2007-117611, and Article of Osaka City University 'Ogawa et al. Am J Cardiol 2006; 98: 1531-1538', a strain gauge display method of displaying a 'strain gauge' connecting the pair between two points for strain measurement, for example, using the speckle tracking has been proposed.

In the known methods, however, a state of movement of the line segment between two points which connects the position of the endomyocardial layer with the position of the epimyocardial layer is displayed by strain gauges on only one plane. For this reason, the heart wall motion showing three-dimensional complicated movement may not be sufficiently observed.

BRIEF SUMMARY OF THE INVENTION

In view of the above, it is an object of the invention to provide an ultrasonic diagnostic apparatus, an ultrasonic image processing apparatus, and a medical image processing apparatus capable of sufficiently observing a state of the motion of tissue, which shows three-dimensional complicated movement and is represented by the heart, by setting a gauge for performing strain measurement in three-dimensional data and imaging it.

According to an aspect of the invention, an ultrasonic diagnostic apparatus includes: a data collection unit that collects volume data over one or more periods of movement of tissue of a subject body, which moves periodically, by ultrasonically scanning the tissue of the subject body; an interest region setting unit that sets a three-dimensional region of interest of the tissue of the subject body for the volume data in a predetermined time phase; a motion vector information generating unit that generates motion vector information on the region of interest in time phases other than the predetermined time phase by processing using pattern matching; a gauge setting unit that sets at least one three-dimensional position of a strain gauge, which is a line segment on the tissue of the subject body, using the motion vector information on the region of interest; an image generating unit that generates a three-dimensional strain gauge image obtained by imaging the set strain gauge in a three-dimensional manner; and a display unit that displays the three-dimensional strain gauge image in a predetermined form.

According to another aspect of the invention, an ultrasonic diagnostic apparatus includes: a data collection unit that collects volume data over one or more periods of movement of tissue of a subject body, which moves periodically, by ultrasonically scanning the tissue of the subject body; an interest region setting unit that sets a three-dimensional region of interest of the tissue of the subject body for the volume data in a predetermined time phase; a motion vector information generating unit that generates motion vector information on the region of interest in time phases other than the predetermined time phase by processing using pattern matching; a gauge setting unit that sets at least one three-dimensional position of a strain gauge, which is a line segment on the tissue of the subject body, using the motion vector information on the region of interest; a section setting unit that sets at least one arbitrary section for volume data in each time phase; an image generating unit that generates a three-dimensional strain gauge image obtained by projection of the strain gauge onto at least the one arbitrary section; and a display unit that displays the three-dimensional strain gauge image in a predetermined form.

According to yet another aspect of the invention, an ultrasonic diagnostic apparatus includes: a data collection unit that collects volume data over one or more periods of movement of tissue of a subject body, which moves periodically, by ultrasonically scanning the tissue of the subject body; a section setting unit that sets at least one arbitrary section for volume data in each time phase; an interest region setting unit that sets a region of interest of the tissue of the subject body on at least the one arbitrary section in a predetermined time phase; a motion vector information generating unit that generates motion vector information on the region of interest in time phases other than the predetermined time phase by processing using pattern matching; a gauge setting unit that sets at least one three-dimensional position of a strain gauge, which is a line segment on the tissue of the subject body, using the motion vector information on the region of interest; an image generating unit that generates a three-dimensional strain gauge image in which the strain gauge is set at a corresponding position on at least the one arbitrary section; and a display unit that displays the three-dimensional strain gauge image in a predetermined form.

According to yet another aspect of the invention, an ultrasonic image processing apparatus includes: a storage unit that stores volume data collected over one or more periods of movement of tissue of a subject body, which moves periodically, by ultrasonically scanning the tissue of the subject body; an interest region setting unit that sets a three-dimensional region of interest of the tissue of the subject body for the volume data in a predetermined time phase; a motion vector information generating unit that generates motion vector information on the region of interest in time phases other than the predetermined time phase by processing using pattern matching; a gauge setting unit that sets at least one three-dimensional position of a strain gauge, which is a line segment on the tissue of the subject body, using the motion vector information on the region of interest; an image generating unit that generates a three-dimensional strain gauge image obtained by imaging the set strain gauge in a three-dimensional manner; and a display unit that displays the three-dimensional strain gauge image in a predetermined form.

According to yet another aspect of the invention, an ultrasonic image processing apparatus includes: a storage unit that stores volume data collected over one or more periods of movement of tissue of a subject body, which moves periodically, by ultrasonically scanning the tissue of the subject body; an interest region setting unit that sets a three-dimensional region of interest of the tissue of the subject body for the volume data in a predetermined time phase; a motion vector information generating unit that generates motion vector information on the region of interest in time phases other than the predetermined time phase by processing using pattern matching; a gauge setting unit that sets at least one three-dimensional position of a strain gauge, which is a line segment on the tissue of the subject body, using the motion vector information on the region of interest; a section setting unit that sets at least one arbitrary section for volume data in each time phase; an image generating unit that generates a three-dimensional strain gauge image obtained by projection of the strain gauge onto at least the one arbitrary section; and a display unit that displays the three-dimensional strain gauge image in a predetermined form.

According to yet another aspect of the invention, an ultrasonic image processing apparatus includes: a storage unit that stores volume data collected over one or more periods of movement of tissue of a subject body, which moves periodically, by ultrasonically scanning the tissue of the subject body; a section setting unit that sets at least one arbitrary section for volume data in each time phase; an interest region setting unit that sets a region of interest of the tissue of the subject body on at least the one arbitrary section in a predetermined time phase; a motion vector information generating unit that generates motion vector information on the region of interest in time phases other than the predetermined time phase by processing using pattern matching; a gauge setting unit that sets at least one three-dimensional position of a strain gauge, which is a line segment on the tissue of the subject body, using the motion vector information on the region of interest; an image generating unit that generates a three-dimensional strain gauge image in which the strain gauge is set at a corresponding position on at least the one arbitrary section; and a display unit that displays the three-dimensional strain gauge image in a predetermined form.

According to yet another aspect of the invention, a medical image processing apparatus includes: a storage unit that stores volume data collected for tissue of a subject body, which moves periodically, over one or more periods; an interest region setting unit that sets a three-dimensional region of interest of the tissue of the subject body for the volume data in a predetermined time phase; a motion vector information generating unit that generates motion vector information on the region of interest in time phases other than the predetermined time phase by processing using pattern matching; a gauge setting unit that sets at least one three-dimensional position of a strain gauge, which is a line segment on the tissue of the subject body, using the motion vector information on the region of interest; an image generating unit that generates a three-dimensional strain gauge image obtained by imaging the set strain gauge in a three-dimensional manner; and a display unit that displays the three-dimensional strain gauge image in a predetermined form.

According to yet another aspect of the invention, a medical image processing apparatus includes: a storage unit that stores volume data collected for tissue of a subject body, which moves periodically, over one or more periods; an interest region setting unit that sets a three-dimensional region of interest of the tissue of the subject body for the volume data in a predetermined time phase; a motion vector information generating unit that generates motion vector information on the region of interest in time phases other than the predetermined time phase by processing using pattern matching; a gauge setting unit that sets at least one three-dimensional position of a strain gauge, which is a line segment on the tissue of the subject body, using the motion vector information on the region of interest; a section setting unit that sets at least one arbitrary section for volume data in each time phase; an image generating unit that generates a three-dimensional strain gauge image obtained by projection of the strain gauge onto at least the one arbitrary section; and a display unit that displays the three-dimensional strain gauge image in a predetermined form.

According to yet another aspect of the invention, a medical image processing apparatus includes: a storage unit that stores volume data collected for tissue of a subject body, which moves periodically, over one or more periods; a section setting unit that sets at least one arbitrary section for volume data in each time phase; an interest region setting unit that sets a region of interest of the tissue of the subject body on at least the one arbitrary section in a predetermined time phase; a motion vector information generating unit that generates motion vector information on the region of interest in time phases other than the predetermined time phase by processing using pattern matching; a gauge setting unit that sets at least one three-dimensional position of a strain gauge, which is a line segment on the tissue of the subject body, using the motion vector information on the region of interest; an image generating unit that generates a three-dimensional strain gauge image in which the strain gauge is set at a corresponding position on at least the one arbitrary section; and a display unit that displays the three-dimensional strain gauge image in a predetermined form.

According to yet another aspect of the invention, an ultrasonic image generating method includes: collecting volume data over one or more periods of movement of tissue of a subject body, which moves periodically, by ultrasonically scanning the tissue of the subject body; setting a three-dimensional region of interest of the tissue of the subject body for the volume data in a predetermined time phase; generating motion vector information on the region of interest in time phases other than the predetermined time phase by processing using pattern matching; setting at least one three-dimensional position of a strain gauge, which is a line segment on the tissue of the subject body, using the motion vector information on the region of interest; generating a three-dimensional strain gauge image obtained by imaging the set strain gauge in a three-dimensional manner; and displaying the three-dimensional strain gauge image in a predetermined form.

According to yet another aspect of the invention, an ultrasonic image generating method includes: collecting volume data over one or more periods of movement of tissue of a subject body, which moves periodically, by ultrasonically scanning the tissue of the subject body; setting a three-dimensional region of interest of the tissue of the subject body for the volume data in a predetermined time phase; generating motion vector information on the region of interest in time phases other than the predetermined time phase by processing using pattern matching; setting at least one three-dimensional position of a strain gauge, which is a line segment on the tissue of the subject body, using the motion vector information on the region of interest; setting at least one arbitrary section for volume data in each time phase; generating a three-dimensional strain gauge image obtained by projection of the strain gauge onto at least the one arbitrary section; and displaying the three-dimensional strain gauge image in a predetermined form.

According to yet another aspect of the invention, an ultrasonic image generating method includes: collecting volume data over one or more periods of movement of tissue of a subject body, which moves periodically, by ultrasonically scanning the tissue of the subject body; setting at least one arbitrary section for volume data in each time phase; setting a region of interest of the tissue of the subject body on at least the one arbitrary section in a predetermined time phase; generating motion vector information on the region of interest in time phases other than the predetermined time phase by processing using pattern matching; setting at least one three-dimensional position of a strain gauge, which is a line segment on the tissue of the subject body, using the motion vector information on the region of interest; generating a three-dimensional strain gauge image in which the strain gauge is set at a corresponding position on at least the one arbitrary section; and displaying the three-dimensional strain gauge image in a predetermined form.

According to yet another aspect of the invention, an ultrasonic image processing method includes: storing volume data collected over one or more periods of movement of tissue of a subject body, which moves periodically, by ultrasonically scanning the tissue of the subject body; setting a three-dimensional region of interest of the tissue of the subject body for the volume data in a predetermined time phase; generating motion vector information on the region of interest in time phases other than the predetermined time phase by processing using pattern matching; setting at least one three-dimensional position of a strain gauge, which is a line segment on the tissue of the subject body, using the motion vector information on the region of interest; generating a three-dimensional strain gauge image obtained by imaging the set strain gauge in a three-dimensional manner; and displaying the three-dimensional strain gauge image in a predetermined form.

According to yet another aspect of the invention, an ultrasonic image processing method includes: storing volume data collected over one or more periods of movement of tissue of a subject body, which moves periodically, by ultrasonically scanning the tissue of the subject body; setting a three-dimensional region of interest of the tissue of the subject body for the volume data in a predetermined time phase; generating motion vector information on the region of interest in time phases other than the predetermined time phase by processing using pattern matching; setting at least one three-dimensional position of a strain gauge, which is a line segment on the tissue of the subject body, using the motion vector information on the region of interest; setting at least one arbitrary section for volume data in each time phase; generating a three-dimensional strain gauge image obtained by projection of the strain gauge onto at least the one arbitrary section; and displaying the three-dimensional strain gauge image in a predetermined form.

According to yet another aspect of the invention, an ultrasonic image processing method includes: storing volume data collected over one or more periods of movement of tissue of a subject body, which moves periodically, by ultrasonically scanning the tissue of the subject body; setting at least one arbitrary section for volume data in each time phase; setting a region of interest of the tissue of the subject body on at least the one arbitrary section in a predetermined time phase; generating motion vector information on the region of interest in time phases other than the predetermined time phase by processing using pattern matching; setting at least one three-dimensional position of a strain gauge, which is a line segment on the tissue of the subject body, using the motion vector information on the region of interest; generating a three-dimensional strain gauge image in which the strain gauge is set at a corresponding position on at least the one arbitrary section; and displaying the three-dimensional strain gauge image in a predetermined form.

According to yet another aspect of the invention, a medical image processing method includes: storing volume data collected for tissue of a subject body, which moves periodically, over one or more periods; setting a three-dimensional region of interest of the tissue of the subject body for the volume data in a predetermined time phase; generating motion vector information on the region of interest in time phases other than the predetermined time phase by processing using pattern matching; setting at least one three-dimensional position of a strain gauge, which is a line segment on the tissue of the subject body, using the motion vector information on the region of interest; generating a three-dimensional strain gauge image obtained by imaging the set strain gauge in a three-dimensional manner; and displaying the three-dimensional strain gauge image in a predetermined form.

According to yet another aspect of the invention, a medical image processing method includes: storing volume data collected for tissue of a subject body, which moves periodically, over one or more periods; setting a three-dimensional region of interest of the tissue of the subject body for the volume data in a predetermined time phase; generating motion vector information on the region of interest in time phases other than the predetermined time phase by processing using pattern matching; setting at least one three-dimensional position of a strain gauge, which is a line segment on the tissue of the subject body, using the motion vector information on the region of interest; setting at least one arbitrary section for volume data in each time phase; generating a three-dimensional strain gauge image obtained by projection of the strain gauge onto at least the one arbitrary section; and displaying the three-dimensional strain gauge image in a predetermined form.

According to yet another aspect of the invention, a medical image processing method includes: storing volume data collected for tissue of a subject body, which moves periodically, over one or more periods; setting at least one arbitrary section for volume data in each time phase; setting a region of interest of the tissue of the subject body on at least the one arbitrary section in a predetermined time phase; generating motion vector information on the region of interest in time phases other than the predetermined time phase by processing using pattern matching; setting at least one three-dimensional position of a strain gauge, which is a line segment on the tissue of the subject body, using the motion vector information on the region of interest; generating a three-dimensional strain gauge image in which the strain gauge is set at a corresponding position on at least the one arbitrary section; and displaying the three-dimensional strain gauge image in a predetermined form.

BRIEF DESCRIPTION OF THE SEVERAL VIEWS OF THE DRAWING

FIG. 6 is a view illustrating a three-dimensional strain gauge image, in which only a strain gauge set on a 4C-plane image in the reference time phase is extracted, together with an MPR image in the reference time phase;

FIG. 7 is a view illustrating a three-dimensional strain gauge image, in which only a strain gauge set on a 2C-plane image in the reference time phase is extracted, together with an MPR image in the reference time phase;

FIG. 8 is a view illustrating a three-dimensional strain gauge image, in which strain gauges set on A-plane image, M-plane image, and B-plane image in the reference time phase are extracted, together with an MPR image in the reference time phase;

DETAILED DESCRIPTION OF THE INVENTION

Figure 1:
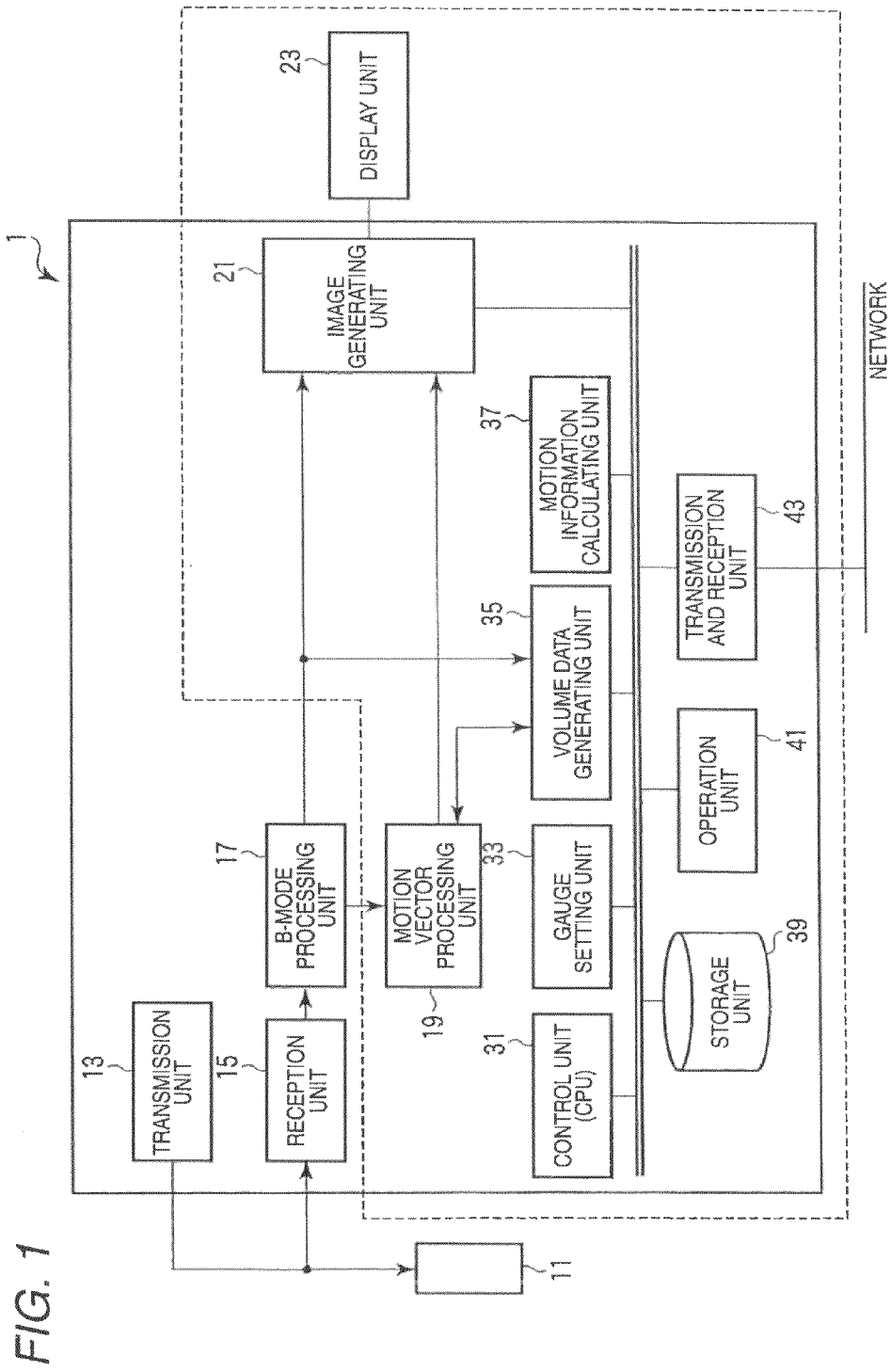
FIG. 1 is a block diagram illustrating an ultrasonic diagnostic apparatus according to a first embodiment.

Hereinafter, embodiments of the invention will be described with reference to the accompanying drawings. Moreover, in the following description, constituent components having approximately the same function and configuration are denoted by the same reference numeral, and a repeated explanation thereof will only be made as needed.

In addition, in each embodiment to be described below, a case where the technical idea of the invention is applied to an ultrasonic diagnostic apparatus will be described as an example. However, the invention does not need to be limited to the ultrasonic diagnostic apparatus, and the technical idea of the invention may also be applied to an ultrasonic image processing apparatus using a workstation, a personal computer, etc., a medical image processing apparatus using a medical image, such as a CT image or an MRI image, and a medical image diagnostic apparatus (for example, an apparatus for X-ray computerized tomography and a magnetic resonance imaging apparatus) other than the ultrasonic diagnostic apparatus.

Moreover, functions realized by constituent components in each embodiment, in particular, functions realized by a motion vector processing unit 19, an image generating unit 21, a tracking processing unit 33, a motion information calculating unit 37, and a gauge setting unit 38 (refer to FIG. 1) which will be described later may be realized by installing a software program for executing the same processing as each of the constituent components in a computer such as a workstation, an ultrasonic diagnostic apparatus having a computer function, and the like and then loading the software program into a memory. In this case, a program capable of causing a computer to execute a corresponding technique may be distributed in a state where the program is stored in a recording medium, such as a magnetic disk (for example, a floppy (registered trademark) disk or a hard disk), an optical disk (for example, a CD-ROM or a DVD), and a semiconductor memory.

(First Embodiment)

FIG. 1 is a block diagram illustrating an ultrasonic diagnostic apparatus 1 according to a first embodiment. The ultrasonic diagnostic apparatus 1 includes an ultrasonic probe 11, a transmission unit 13, a reception unit 15, a B-mode processing unit 17, the motion vector processing unit 19, the image generating unit 21, a display unit 23, a control unit (CPU) 31, a volume data generating unit 35, the motion information generating unit 37, the gauge setting unit 38, a storage unit 39, an operation unit 41, and a network transmission and reception unit 43. In addition, in the case of applying the technical idea of the invention to an ultrasonic image processing apparatus, the inside components of a dotted line of FIG. 1 are constituent components of the ultrasonic image processing apparatus, for example.

The ultrasonic probe 11 generates an ultrasonic wave on the basis of a driving signal from the transmission unit 12 and has a plurality of piezoelectric vibrators that convert reflected waves from a subject body into electric signals, a matching layer provided in the piezoelectric vibrators, a packing material that prevents rearward propagation of an ultrasonic wave from the piezoelectric vibrators, and the like. When an ultrasonic wave is transmitted from the ultrasonic probe 11 to the subject body, various harmonic components are generated with propagation of an ultrasonic wave due to nonlinearity of the body tissue. A fundamental wave and harmonic components which form the transmitted ultrasonic wave are scattered rearward by the boundary of the acoustic impedance of the body tissue, minute scattering, and the like and are received as a reflected wave (echo) in the ultrasonic probe 11.

The transmission unit 13 has a delay circuit, a pulse circuit, and the like which are not shown. The pulse circuit repeatedly generates a rate pulse for forming a transmitted ultrasonic wave at a predetermined rate frequency fr Hz (period; 1/fr second). In addition, in the delay circuit, a delay time which is required for making ultrasonic waves converge in the beam shape and determining the transmission directivity for every channel is given to each rate pulse. The transmission unit 12 applies a driving pulse to every vibrator, at timing based on the rate pulse, such that an ultrasonic beam is formed toward a predetermined scan line.

The reception unit 15 has an amplifying circuit, an A/D converter, an adder, and the like which are not shown. The amplifying circuit amplifies an echo signal received through the probe 11 for every channel. The A/D converter gives a delay time, which is required for determining the receiving directivity, to the amplified echo signal, and then the adder performs adding processing. By this addition, an ultrasonic echo signal corresponding to the predetermined scan line is generated.

The B-mode processing unit 17 generates a B-mode signal corresponding to the amplitude of an ultrasonic echo by performing envelope detection processing on the ultrasonic echo signal received from the reception unit 15.

The motion vector processing unit 19 detects and tracks the tissue position using pattern matching processing between two frames with different time phases and calculates the displacement of each tissue on the basis of the moved position. Specifically, the motion vector processing unit 19 calculates, for a region of interest on one frame, a corresponding region on another frame which is most similar to the region of interest. The total displacement of the tissue can be defined by accumulating a distance between the region of interest and the corresponding region which estimated by motion vector processing unit. By performing this processing frame by frame at each position on a frame, displacement (motion vector) of each tissue or spatial-temporal distribution data regarding displacement of tissue can be acquired.

The image generating unit 21 generates a B-mode ultrasonic image showing dimensional distribution related to a predetermined reconstruction of a B-mode signal. In addition, the image generating unit 21 generates a B-mode ultrasonic image, an image regarding motion information of tissue, a superimposed image of the B-mode ultrasonic image and the image regarding motion information of tissue, and the like. Here, the motion information of the tissue is physical information which may be acquired regarding the motion of the tissue other than strain, strain rate, displacement, and velocity of the tissue. Hereinafter, an image including such motion information of the tissue is generally called a 'motion information image'.

The display unit 23 displays morphological information or motion information in the body, on the basis of a video signal from the image generating unit 21, as an image in a predetermined form. In addition, the display unit 23 displays markers for supporting matching of the positions between images in the case of displaying a plurality of images.

The control unit (CPU) 31 has a function as an information processing device (computer) and statically or dynamically controls an operation of a main body of the ultrasonic diagnostic apparatus. In particular, the control unit 31 realizes an arbitrary section tracking function, which will be described later, by loading an exclusive program stored in the storage unit 39 into a memory (not shown).

The volume data generating unit 35 executes spatial interpolation processing using B-mode data for every frame, which is received from the B-mode processing unit 17, and spatial distribution data of tissue displacement for every time phase, which is received from the motion vector processing unit 19, and generates volume data on a diagnostic subject, which moves periodically, for each time phase regarding the periodic movement. Moreover, in the present embodiment, it is assumed that the volume data generating unit 35 generates volume data using data (so-called raw data) in a preceding stage compared with the image generating unit 21. However, the volume data generating unit 35 may be configured to generate volume data using data (so-called image data) in a subsequent stage compared with the image generating unit 21, without being limited to that described above.

The motion information calculating unit 37 calculates various kinds of motion information (for example, displacement, velocity, strain, a strain rate, torsion, and a difference of rotation components between endomyocardial and epimyocardial layers) using each coordinate of the tissue for every time phase acquired by the motion vector processing unit 19.

The gauge setting unit 38 executes processing, such as strain gauge setting to be described later, using the motion vector information output from the motion vector processing unit 19.

The storage unit 39 is a recording medium, such as a magnetic disk (for example, a floppy (registered trademark) disk or a hard disk), an optical disk (for example, a CD-ROM, a DVD), and a semiconductor memory, and is a device that reads information recorded in these recording media. Transmission and reception conditions, a predetermined scan sequence, raw data and ultrasonic image data (for example, tissue image data photographed in a tissue Doppler mode, a B mode, etc.) corresponding to each time phase, volume data for every time phase generated in the volume data generating unit 35, various kinds of motion information acquired, an exclusive program for realizing a motion vector calculating function, a control program for executing generation and display of a three-dimensional strain gauge image, diagnostic information (for example, a patient ID and doctor's opinion), a diagnostic protocol, a body mark generating program, and the like are stored in the storage unit 39.

The operation unit 41 is connected to the main body of the apparatus and has a mouse or a trackball, a mode switch, a keyboard, and the like for importing to the main body of the apparatus various instructions from an operator, such as an instruction for setting a region of interest (ROI) and an instruction for setting various conditions on the image quality, designation of a reference time phase in arbitrary section tracking processing, setting of an arbitrary section in the reference time phase, and the like.

The transmission and reception unit 43 is a device which transmits information to another apparatus or receives information from another apparatus through a network. Data or an analysis result of an ultrasonic image obtained in the ultrasonic diagnostic apparatus 1 may be transmitted to another apparatus through the network by the transmission and reception unit 43.

(Function of generation and display of a three-dimensional strain gauge image)

Next, a function of generation and display of a three-dimensional strain gauge image that the ultrasonic diagnostic apparatus 1 has will be described. This function is to generate a line segment (gauge) for visually showing the reigional strain of the cardiac muscle and to display it at the corresponding position on an ultrasonic image in a three-dimensional manner.

Moreover, in the present embodiment, a motion information generating function when a diagnostic subject is the heart will be described as an example in order to make a specific explanation. However, a subject to which the motion information generating function is applied is not limited to the heart, and the motion information generating function may be applied to any part as long as the part substantially moves periodically.

Figure 2:
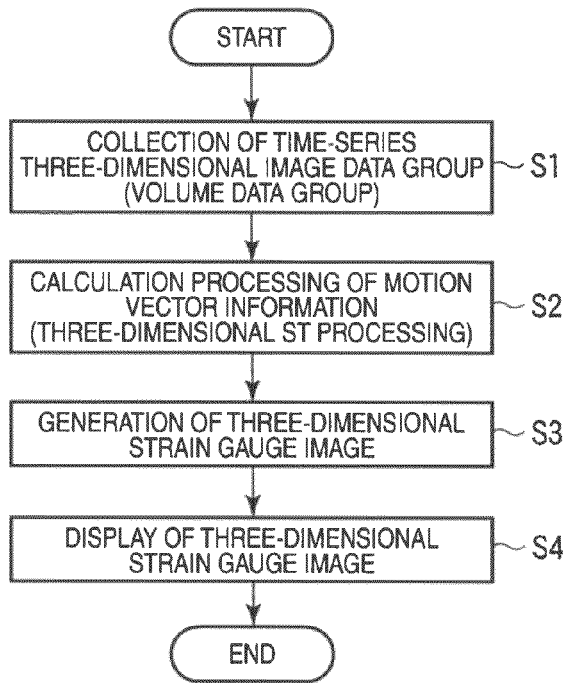
FIG. 2 is a flow chart illustrating the flow of processing for generating and displaying a three-dimensional strain gauge image in the first embodiment.

FIG. 2 is a flow chart illustrating the flow of processing (processing for generating and displaying a three-dimensional strain gauge image) based on the function of generation and display of a three-dimensional strain gauge image. Hereinafter, an explanation will be made with reference to FIG. 2.

[Step S1: Data Collection]

First, for a desired observation portion of the heart of a certain patient, time-series three-dimensional image data (volume data; hereinafter, referred to as a 'time-series volume data group') is collected over a period of at least one cardiac beat using a predetermined time as a reference time (step S1). In addition, the volume data collection method is not particularly limited to one method. For example, volume scan may be performed using any one of a one-dimensional array probe with mechanical scan or a two-dimensional array probe. Alternatively, it may be possible to use three-dimensional triggered scan of generating volume data regarding a desired range by connecting sub-volume data regarding a small region, which was collected in synchronization with ECG, on the basis of a matched trigger and of sequentially updating the sub-volume data according to time information.

[Step S2: Calculation Processing of Motion Vector Information]

Next, motion vector information of tissue in each time phase is generated (step S2). That is, the motion vector processing unit 19 calculates spatial-temporal motion vector information by extracting a region of interest of a myocardial portion from volume data in predetermined time phase, among volume data corresponding to each time phase of one or more cardiac beats which forms a time-series volume data group collected, in response to the user's instruction or the like and by tracking the extracted region of interest temporally by three-dimensional pattern matching processing (speckle tracking processing: ST processing).

[Step S3: Generation of a Three-Dimensional Strain Gauge Image]

Then, processing for generating a three-dimensional strain gauge image is executed (step S3).

Figure 3:
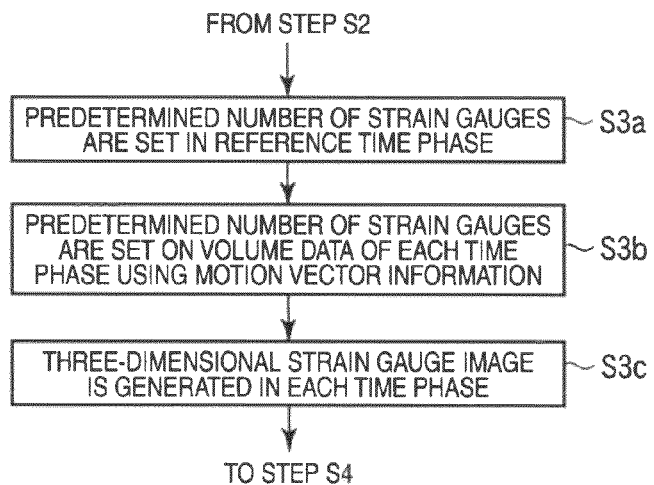
FIG. 3 is a flow chart illustrating the flow of processing executed to generate a strain gauge image.

FIG. 3 is a flow chart illustrating the flow of processing executed to generate a strain gauge image. As shown in FIG. 3, the gauge setting unit 36 sets a predetermined number of (for example, about tens of) strain gauges for an ultrasonic image corresponding to the time phase (for example, time phase of end-systole as a reference time phase) as a reference (step S3a).

That is, the gauge setting unit 36 displays five MPR images of two B-mode images (apical four-chamber image: 4C, apical two-chamber image: 2C) and three C-mode images (apical level: A (Apical), middle level: M (Mid), basal level: B (Basal); hereinafter, apical level: A (Apical), middle level: M (Mid), and basal level: B (Basal) are simply referred to as A plane, M plane, and B plane, respectively), for example, sets the initial outline at positions of endomyocardial and epimyocardial layers on each MPR image in the time phase of end-systole, and sets one sides of a number of gauge endpoints set beforehand at predetermined distances (or at equal angles with the center of gravity of the endomyocardial layer as the center) on the initial outline. In addition, the gauge setting unit 36 sets a plurality of strain gauges by setting the positions, at which the normal vector with respect to the endomyocardial layer surface at one side of each gauge endpoint on the initial outline crosses the epimyocardial layer, as other sides of the gauge endpoints and connecting the gauge endpoints with each other as a line segment (strain gauge) along the normal vector.

Then, the gauge setting unit 36 sets each strain gauge for volume data in another time phase by using motion vector information and each strain gauge set in the reference time phase (step S3b). That is, the gauge setting unit 36 sets each corresponding strain gauge on volume data in each time phase by tracking a gauge endpoint, which forms each strain gauge set in the reference time phase, using the motion vector information.

Then, the image generating unit 21 generates a strain gauge image for every time phase, in which each strain gauge is disposed at a corresponding position of the ultrasonic image, by rendering processing or the like. (step S3c).

[Step S4: Display of a Strain Gauge Image]

Then, the display unit 23 displays a three-dimensional strain gauge image in a predetermined form (step S4).

Figure 4:
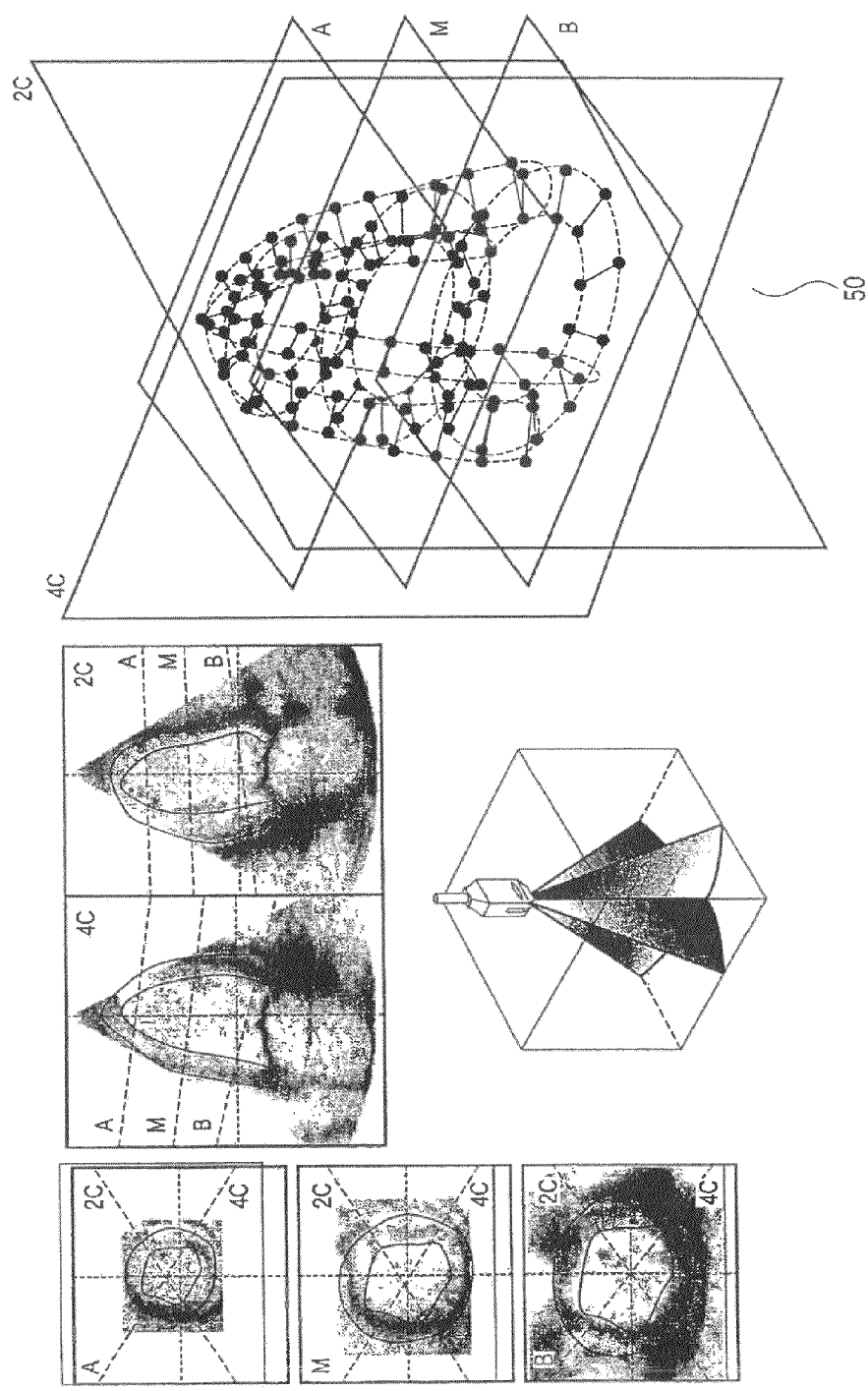
FIG. 4 is a view illustrating an example of a three-dimensional strain gauge image displayed on a display unit.

FIG. 4 is a view illustrating an example of a three-dimensional strain gauge image displayed on the display unit 23. On a three-dimensional strain gauge image 50 shown in FIG. 4, strain gauges set for the five MPR images of two planes (4C, 2C) of a B-mode image and three planes (A plane, M plane, B plane) of a C-mode image in the reference time phase are displayed sparsely so that they are easily observed among a plurality of strain gauges set within a region of interest of the myocardium.

In the case of displaying the three-dimensional strain gauge image 50 continuously with time-series, each strain gauge of the three-dimensional strain gauge image 50 exists within each plane of the five MPR images (that is, 4C plane, 2C plane, A plane, M plane, and B plane) in the reference time phase, while the strain gauge of the three-dimensional strain gauge image 50 may arbitrarily protrude from the planes of the five MPR images according to the movement of the tissue in subsequent time phase. Accordingly, in the example shown in FIG. 4, recognition of the anatomical orientation is realized by displaying the three-dimensional strain gauge image 50 in each time phase while showing the positions of the five MPR images in the reference time phase so that the correspondence relationship between each strain gauge on the three-dimensional strain gauge image 50 in each time phase and each strain gauge on the five MPR images in the reference time phase can be easily understood.

In addition, a number of strain gauges may be displayed in high density in a three-dimensional space of the myocardium, for example, without being limited to the example of FIG. 4. However, if easiness in understanding the anatomical orientation or an adverse effect in which displays of strain gauges are interfered with each other so as to be difficult to be seen is taken into consideration, it can be said that the example of FIG. 4 is preferable.

Figure 5:
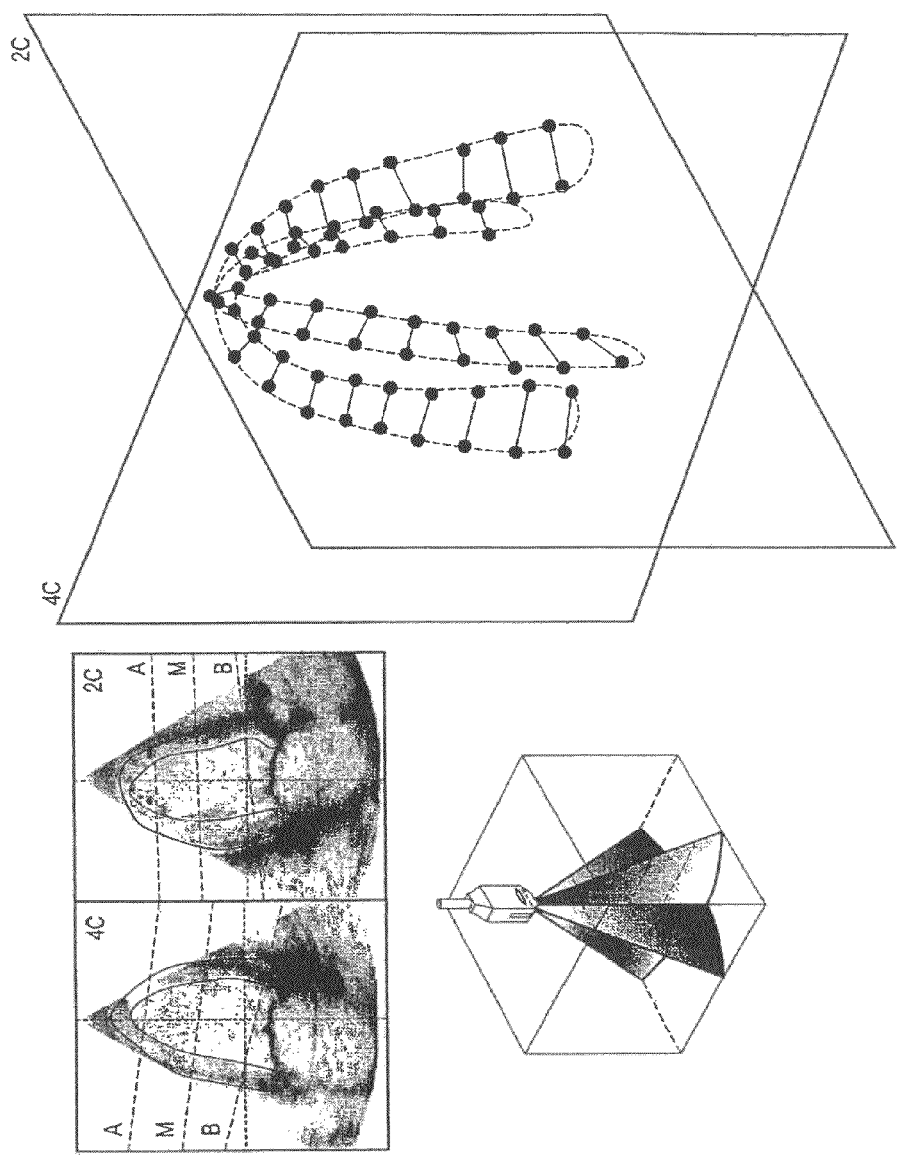
FIG. 5 is a view illustrating a three-dimensional strain gauge image, in which only strain gauges set on 4C and 2C planes in the reference time phase are extracted, together with an MPR image in the reference time phase.
Figure 9:
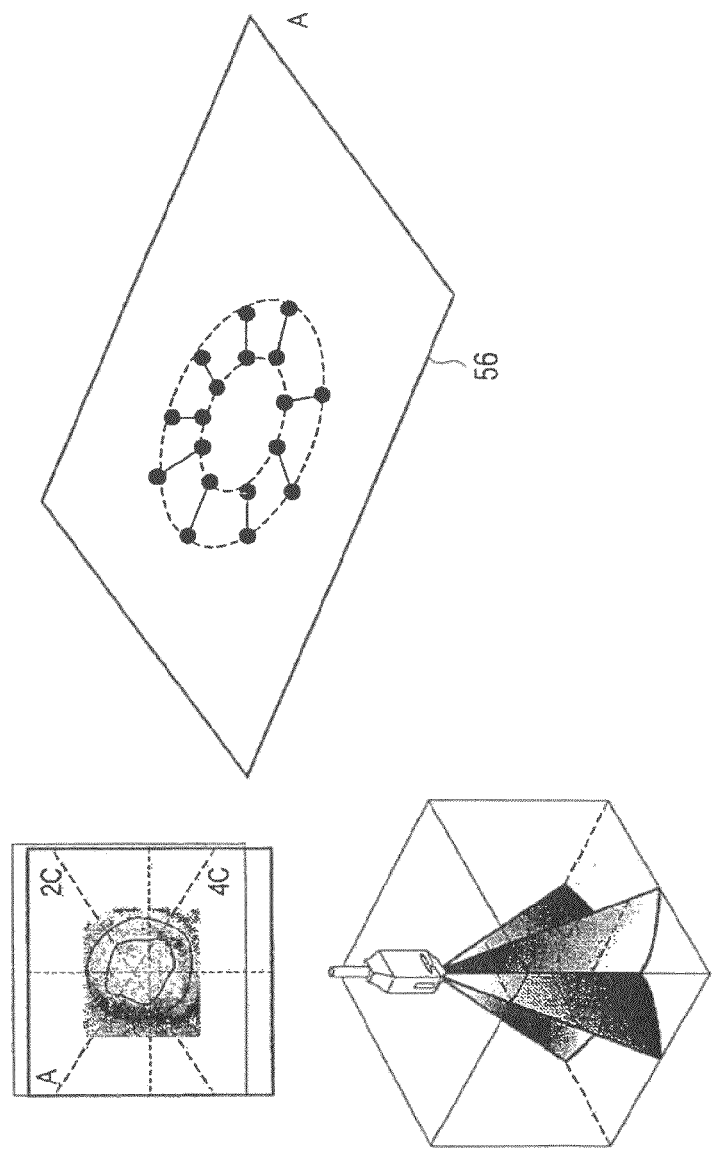
FIG. 9 is a view illustrating a three-dimensional strain gauge image, in which a strain gauge set on the A-plane image in the reference time phase is extracted, together with an MPR image in the reference time phase.
Figure 10:
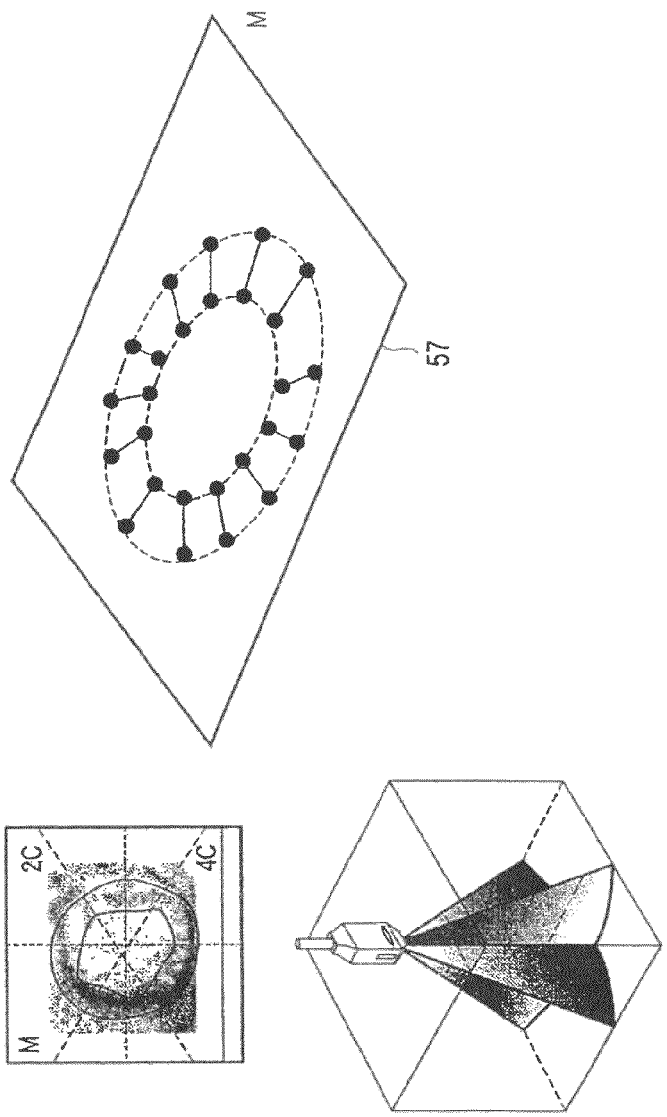
FIG. 10 is a view illustrating a three-dimensional strain gauge image, in which a strain gauge set on the M-plane image in the reference time phase is extracted, together with an MPR image in the reference time phase.
Figure 11:
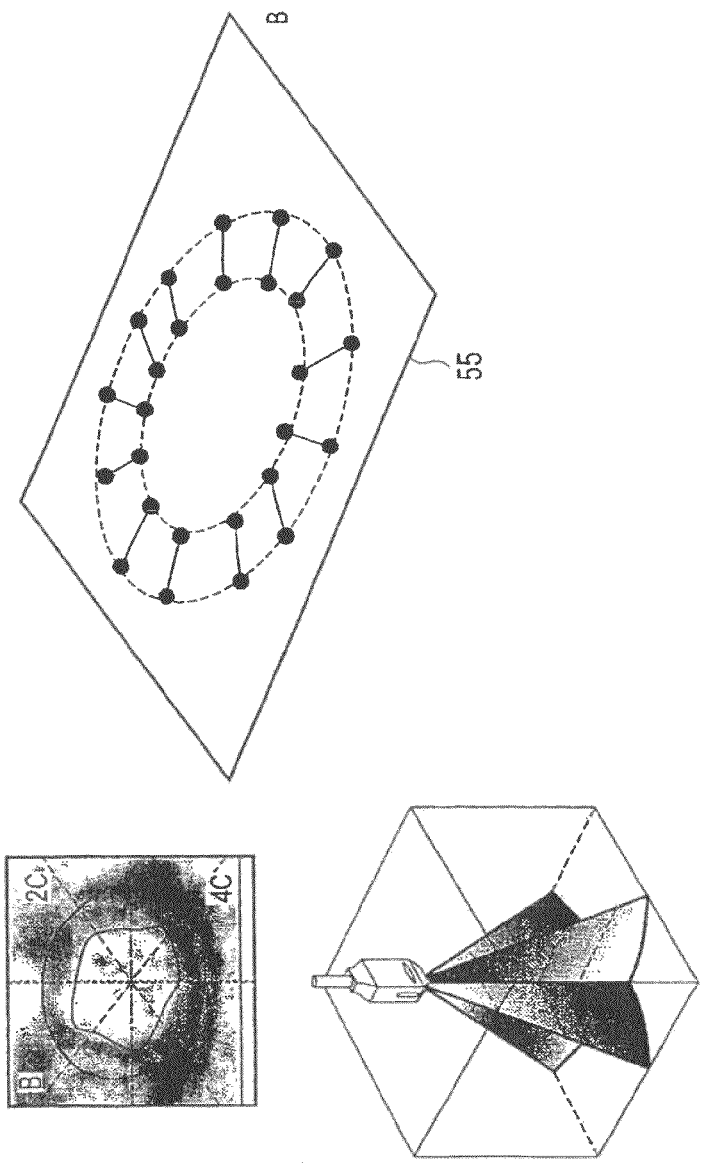
FIG. 11 is a view illustrating a three-dimensional strain gauge image, in which a strain gauge set on the B-plane image in the reference time phase is extracted, together with an MPR image in the reference time phase.

Moreover, three-dimensional strain gauges may be selectively displayed. For example, as shown in FIG. 5, it is possible to generate a three-dimensional strain gauge image 51, in which only strain gauges set on the 4C and 2C planes in the reference time phase are extracted, and to display the three-dimensional strain gauge image 51 together with a 4C-plane image and a 2C-plane image in the reference time phase. In addition, a three-dimensional strain gauge image 52 in which only a strain gauge set on the 4C-plane image in the reference time phase is extracted is displayed in FIG. 6 together with a corresponding MPR image in the reference time phase. A three-dimensional strain gauge image 53 in which only a strain gauge set on the 2C-plane image in the reference time phase is extracted is displayed in FIG. 7 together with a corresponding MPR image in the reference time phase. A three-dimensional strain gauge image 54 in which strain gauges set on the A-plane image, M-plane image, and B-plane image in the reference time phase are extracted is displayed in FIG. 8 together with a corresponding MPR image in the reference time phase. A three-dimensional strain gauge image 55 in which a strain gauge set on the A-plane image in the reference time phase is extracted is displayed in FIG. 9 together with a corresponding MPR image in the reference time phase. A three-dimensional strain gauge image 56 in which a strain gauge set on the M-plane image in the reference time phase is extracted is displayed in FIG. 10 together with a corresponding MPR image in the reference time phase. A three-dimensional strain gauge image 57 in which a strain gauge set on the B-plane image in the reference time phase is extracted is displayed in FIG. 11 together with a corresponding MPR image in the reference time phase.

According to the configuration described above, the following effects can be obtained.

In the ultrasonic diagnostic apparatus, a plurality of strain gauges defined by gauge endpoints are set in each time phase using motion vector information of the tissue and a three-dimensional strain gauge image, in which each strain gauge is disposed at the three-dimensional position corresponding to an ultrasonic image in each time phase, is generated and displayed. The observer can intuitively see not only a change in distance between endomyocardial and epimyocardial layers (change in wall thickness) but also a difference of rotation or displacement between the endomyocardial and epimyocardial layers by observing the three-dimensional strain gauge image displayed. Particularly by observing the three-dimensional behavior of a three-dimensional strain gauge, a situation of wall movement of the heart having a three-dimensional structure can be expressed in a form closer to the actual condition. As a result, the movement which could not be seen in the related art can be checked.

(Second Embodiment)

Next, a second embodiment of the invention will be described. An ultrasonic diagnostic apparatus according to the present embodiment serves to generate and display a three-dimensional strain gauge image with an object to be subjected to speckle tracking processing as a strain gauge between endomyocardial and epimyocardial layers of the heart.

Figure 12:
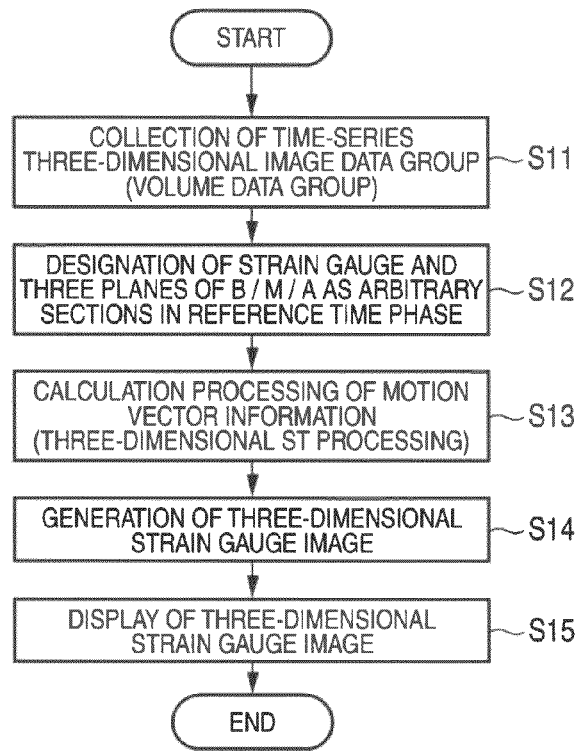
FIG. 12 is a flow chart illustrating the flow of processing for generating and displaying a three-dimensional strain gauge image in a second embodiment.

FIG. 12 is a flow chart illustrating the flow of processing for generating and displaying a three-dimensional strain gauge image in the second embodiment. Hereinafter, details of the processing in each step will be described.

[Step S11: Data Collection]

First, similar to step S1, a time-series volume data group is collected (step S11).

[Step S12: Setting of Arbitrary Section and Strain Gauge]

Then, a plurality of arbitrary sections are set for volume data in a reference time phase, and a strain gauge is set between endomyocardial and epimyocardial layers of the heart on each section (step S12). That is, in reference time phase $t_0$ (for example, time phase of end-diastole or time phase of end-systole) of a period T, for example, three sections of B, M, and A planes are set and a strain gauge is set between the endomyocardial and epimyocardial layers existing on an MPR image corresponding to each section.

Moreover, setting of arbitrary sections for volume data in the reference time phase may be automatically executed using a device or may be manually executed by an operator's input using the operation unit 41. Moreover, for example, the method of step S3a may be used as a method of setting a strain gauge.

[Step S13: Calculation Processing of Motion Vector Information]

Then, the motion vector processing unit 19 calculates motion vector information for every time phase by tracking each section and strain gauge set in the reference time phase $t_0$ by speckle tracking processing and sets each corresponding section for volume data of remaining time phases (that is, each time phase other than the reference time phase $t_0$ in the period T) in which sections and strain gauged were not set in step S12 (step S31).

Moreover, a specific method of tracking an arbitrary section will be described below according to examples.

FIRST EXAMPLE

In a tracking method of this example, a motion component V is calculated by projecting a motion vector at each position of the tissue, which exists on each section, in the normal direction and averaging them and arbitrary sections and strain gauges in each time phase are tracked using the motion component V.

Figure 13:
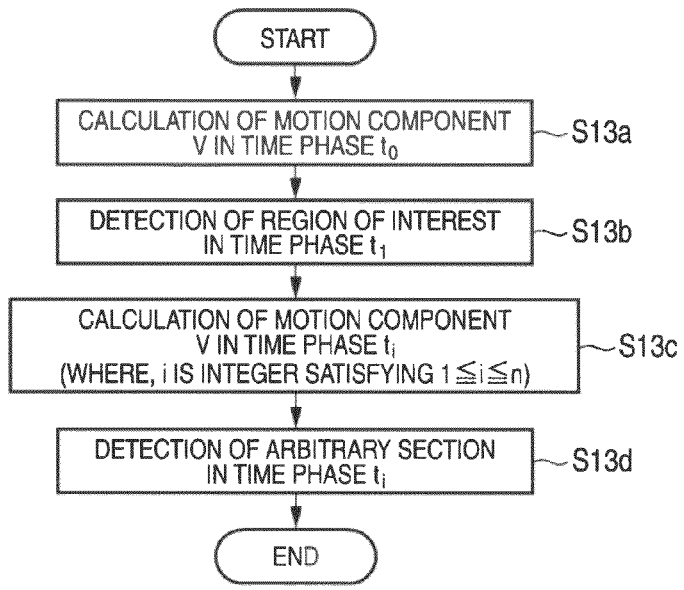
FIG. 13 is a flow chart illustrating the flow of calculation processing of motion vector information in step S13.

FIG. 13 is a flow chart illustrating the flow of calculation processing of motion vector information in step S13. As shown in FIG. 13, first, a motion component $V=V_z$, meant(to) in the reference time phase $t_0$ is calculated by averaging only a normal direction component $V_z$ (projected component in the normal direction) of the motion vector of each myocardium (that is, each position of the tissue included in each plane) on each of the B, M, and A planes set for volume data in the reference time phase (step S13a).

Then, each of the B, M, and A planes set in the reference time phase is moved in parallel by the motion component $V=V_z$, meant($t_0$) along the normal direction to thereby set a heart region included in each of the B, M, and A planes after movement as an arbitrary section in a time phase $t_1$ and set a corresponding strain gauge (step S13b).

Then, a motion component $V=V_z$, meant($t_i$) in a time phase $t_i$ (where, 'i' is an integer satisfying 2≤i≤n) is calculated by averaging only a normal direction component of the motion vector of each myocardium on each of the B, M, and A planes in the time phase $t_i$ (step S13c).

Then, each of the B, M, and A planes in the time phase $t_i$ is moved in parallel by the motion component $V=V_z$, meant($t_i$) along the normal direction to thereby set the B, M, and A planes and corresponding strain gauges in the time phase $t_i$ (step S13d).

Then, B, M, and A planes and strain gauges in each time phase can be tracked by sequentially repeating the processing of steps S13c and S13d in a time-series manner until a time phase $t_n$.

For the B, M, and A planes and the strain gauges tracked by the above-described method in the first example, the positions after movement are detected using the motion component V calculated by averaging only the normal direction component of each position (each myocardium) on each plane. Accordingly, in the method of this example, B, M, and A planes in each time phase are parallel to B, M, and A planes set in the reference time phase, respectively.

SECOND EXAMPLE

In a tracking method of this example, a motion component V is calculated by averaging a motion vector at each position of the tissue existing within a set arbitrary section (without projection in the normal direction) and arbitrary sections and strain gauges in each time phase are tracked using the motion component V.

That is, referring to FIG. 13, first, a motion component $V=V_{mean t}(t_0)$ in the reference time phase to is calculated by averaging a motion vector of each myocardium (that is, each position of the tissue included in each plane) on each of the B, M, and A planes set for volume data in the reference time phase (step S13a).

Then, each of the B, M, and A planes set in the reference time phase is moved in parallel by the motion component $V=V_{meant}(t_0)$ to thereby set B, M, and A planes in a time phase $t_1$ and set a corresponding strain gauge (step S13b).

Then, a motion component $V=V_{meant}(t_i)$ in a time phase $t_i$ (where, 'i' is an integer satisfying $2 \le i \le n$) is calculated by averaging the motion vector of each myocardium on each of the B, M, and A planes in the time phase $t_1$ (step S13c).

Then, each of the B, M, and A planes in the time phase $t_1$ is moved in parallel by the motion component $V=V_{meant}(t_i)$ along the normal direction to thereby set the B, M, and A planes and strain gauges in the time phase $t_i$ (step S13d).

Then, arbitrary sections and strain gauges in each time phase can be tracked by sequentially repeating the processing of steps S13c and S13d in a time-series manner until a time phase $t_n$.

For the B, M, and A planes and the strain gauges tracked by the above-described method in the second example, the positions after movement are detected by using the motion component V calculated by averaging the motion vector of each position (each myocardium) on each plane. Accordingly, in the method of this example, B, M, and A planes in each time phase are not always parallel to B, M, and A planes set in the reference time phase, respectively.

THIRD EXAMPLE

In a tracking method of this example, arbitrary sections and strain gauges in each time phase can be tracked by detecting each position on an arbitrary section in a subsequent time phase using a motion vector for every position of the tissue, which exists within the set arbitrary section, and repeating the detection in a time-series manner.

That is, referring to FIG. 13, first, a motion vector $V=V(j, t_0)$ regarding each position pj(x, y, z) (where, 'j' is an integer satisfying $1 \le j \le m$ and 'm' is the number of positions of myocardial tissues existing on each plane) on each of B, M, and A planes set for volume data in the reference time phase $t_0$ is calculated (step S13a).

Then, a position after moving each position on each of the B, M, and A planes in the reference time phase by the motion vector V=V(j, to) is detected, and planes formed by the positions are set as B, M, and A planes in a subsequent time phase $t_1$ and strain gauges are set (step S13b).

Then, for the positions on the B, M, and A planes in the time phase $t_1$, the motion vector $V=V(j, t_1)$ is calculated (step S13c).

Then, a position after moving each position on each of the B, M, and A planes in the time phase $t_1$ by the motion vector $V=V(j, t_1)$ corresponding to the position is detected, and B, M, and A planes and strain gauges in a subsequent time phase $t_i$ (where, 'i' is an integer satisfying $2 \le i \le n$) are set for the planes formed by the positions (step S13d).

Then, arbitrary sections in each time phase can be tracked by sequentially repeating the processing of steps S13c and S13d in a time-series manner until a time phase $t_n$.

For the B, M, and A planes and strain gauges tracked by the method of the third example, arbitrary sections in each time phase are tracked by detecting each position, which forms each of B, M, and A planes in a subsequent time phase, using a motion vector of each position (each myocardium) on each plane and repeating the detection in a time-series manner. Accordingly, in the method of this example, B, M, and A planes in each time phase become arbitrary curved surfaces in the three-dimensional coordinate system at each time phase after the reference time phase.

In addition, the arrangement of highly precise strain gauges corresponding to more local tracking positions becomes possible in order of the third, second, and first examples.

[Step S14: Generation of a Three-Dimensional Strain Gauge Image]

Then, the image generating unit 21 generates a three-dimensional strain gauge image by projecting a strain gauge, which belongs to an arbitrary section in each time phase, onto a projection plane (step S14). In the case of using the tracking method of the first or second example, as a method of projection of a strain gauge in each tracking method, it is preferable to make a tracked arbitrary section (flat surface in any method) equal to the projection plane.

On the other hand, in the case of the method of the third example, the tracked arbitrary section does not necessarily become a flat surface. Accordingly, it is preferable to calculate a regression plane regarding each fine local position (each position pj (x, y, z) tracked in tracking processing) of the myocardium within the tracked arbitrary section and to reconstruct a three-dimensional strain gauge image using the regression plane as a projection plane. Alternatively, a three-dimensional strain gauge image regarding the regression plane may be generated using data at each position on the regression plane.

[Step S15: Image Display]

Then, the display unit 23 displays a three-dimensional strain gauge image in a predetermined form (step S15).

Figure 14:
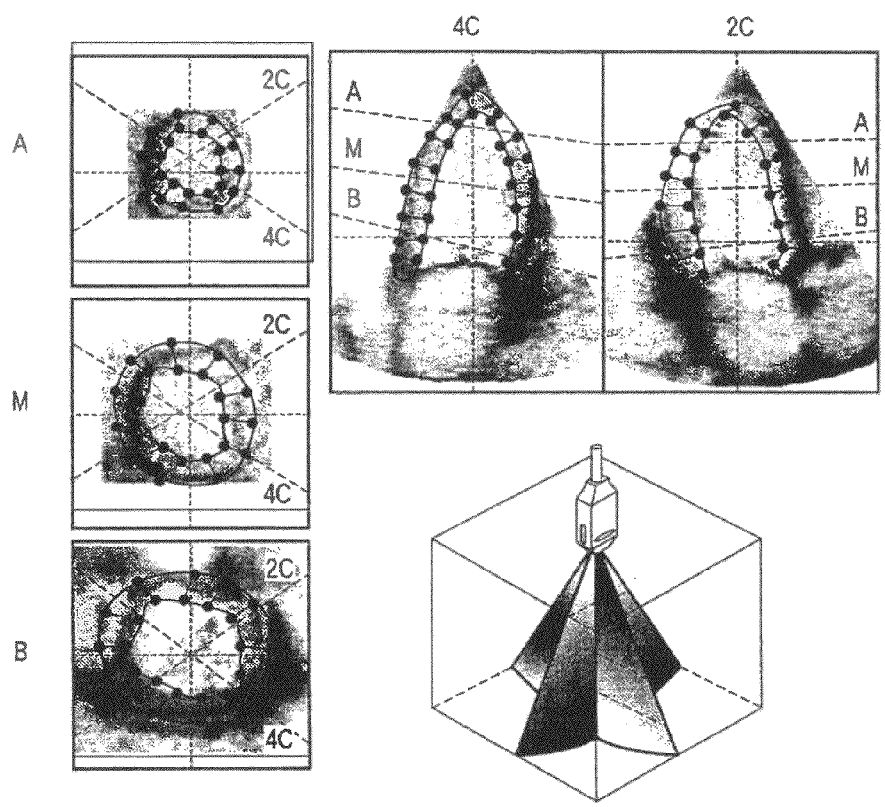
FIG. 14 is a view illustrating an example of a three-dimensional strain gauge image displayed on a display unit.

FIG. 14 is a view illustrating an example of a three-dimensional strain gauge image displayed on the display unit 23. In FIG. 14, five MPR images of an apical four-chamber image (4C image), an apical two-chamber image (2C image), a B-plane image, an M-plane image, and an A-plane image are set and strain gauges are displayed on each MPR image.

(Third Embodiment)

Next, a third embodiment of the invention will be described. An ultrasonic diagnostic apparatus according to the present embodiment is another example of generating and displaying a three-dimensional strain gauge image with an object to be subjected to speckle tracking processing as a strain gauge between endomyocardial and epimyocardial layers of the heart.

Figure 15:
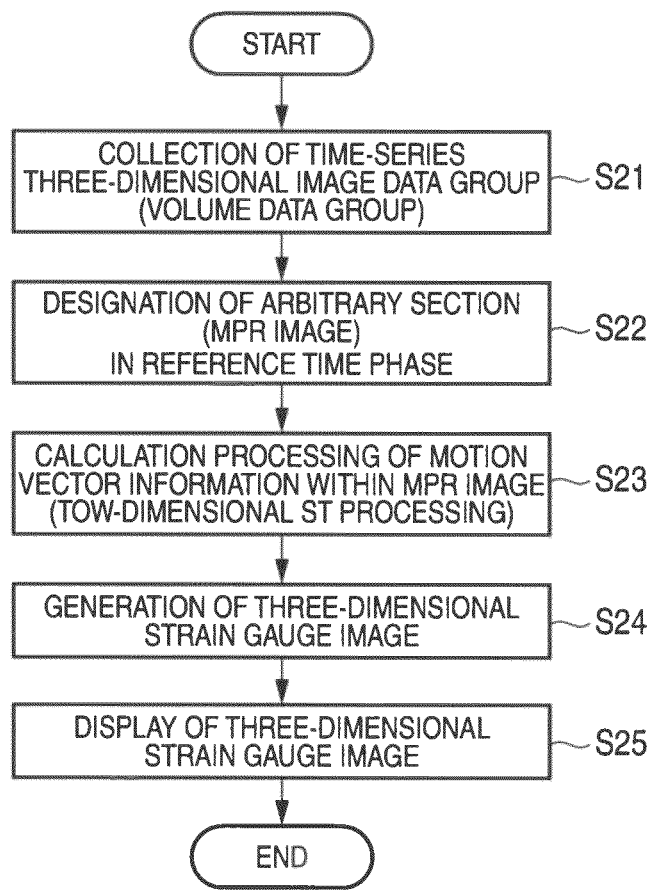
FIG. 15 is a flow chart illustrating the flow of processing for generating and displaying a three-dimensional strain gauge image in a third embodiment.

FIG. 15 is a flow chart illustrating the flow of processing for generating and displaying a three-dimensional strain gauge image in the third embodiment. Hereinafter, details of the processing in each step will be described.

[Step S21: Data Collection]

First, similar to step S1, a time-series volume data group is collected (step S21).

[Step S22: Setting of an Arbitrary Section]

Then, a desired arbitrary section (MPR image may be either singular or plural) is set for volume data in reference time phase $t_0$ (for example, time phase of end-diastole or time phase of end-systole) of the period T (step S22). Setting of the arbitrary section for volume data in the reference time phase may be automatically executed using a device or may be manually executed by an operator's input using the operation unit 41.

[Step S33: Calculation Processing of Motion Vector Information]

Then, the motion vector processing unit 19 executes speckle tracking processing (two-dimensional ST processing) within the MPR image set in the reference time phase to and calculates motion vector information in each time phase of each point corresponding to the tissue (step S33).

[Step S34: Generation of a Three-Dimensional Strain Gauge image]

Then, the image generating unit 21 generates a three-dimensional strain gauge image using the motion vector information for every time phase obtained by the two-dimensional ST processing (step S34). That is, the image generating unit 21 sets a strain gauge in the reference time phase using the method of step S3a, for example, and tracks an endpoint of the strain gauge using the motion vector information for every time phase. As a result, a strain gauge is set on each MPR image in each time phase, and a three-dimensional strain gauge image is generated.

[Step S35: Image Display]

Then, the display unit 23 displays a three-dimensional strain gauge image in a predetermined form (step S35). The three-dimensional strain gauge image obtained by the method in the present embodiment is similar to an example of FIG. 14, for example, when the MPR images set in step S32 are assumed to be five MPR images of two planes (apical four-chamber image: 4C, apical two-chamber image: 2C) of a B-mode image and three planes (A plane, M plane, B plane) of a C-mode image. In addition, display of the three-dimensional strain gauge image using the five MPR images is a suitable example of the method in the present embodiment.

(Fourth Embodiment)

Next, a fourth embodiment of the invention will be described. An ultrasonic diagnostic apparatus according to the present embodiment generates and displays a three-dimensional strain gauge image, in which a gauge midpoint (point existing on the line segment obtained by connecting gauge endpoints) is set in the strain gauge, in the method according to any one of the first to third embodiments. In addition, the gauge midpoint is set as a middle point of the gauge together with endpoints of the strain gauge, for example, in the reference time phase and is tracked in each time phase by tracking processing using motion vector information in steps S3b, S14, and S24.

Figure 16:
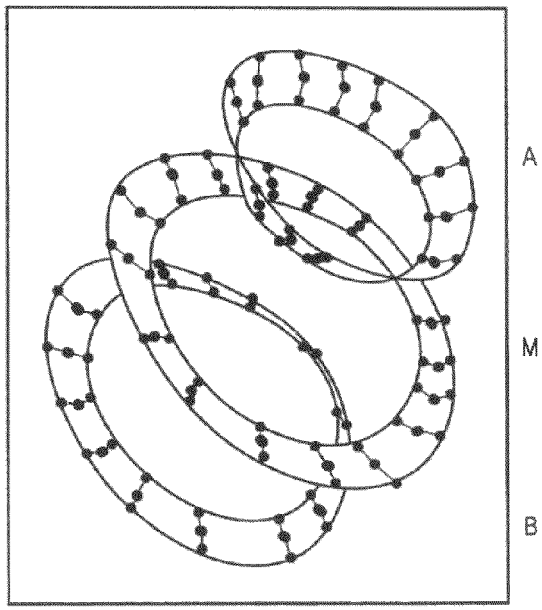
FIG. 16 is a view illustrating an example (short-axis image) of a three-dimensional strain gauge image including a strain gauge in which a midmyocardial layer gauge point is set.

FIG. 16 is a view illustrating an example (short-axis image) of a three-dimensional strain gauge image including a strain gauge in which a gauge midpoint is set. As shown in FIG. 16, it is characteristic that the strain gauge deformed like the line plot with angulation can be observed. This suggests that intuitive recognition of the complicated wall motion resulting from the multi-layered structure of a myocardium can be realized in a three-dimensional manner by the strain gauge having a gauge midpoint. Specifically, it is thought that a result in which endomyocardial layer, midmyocardial layer, and epimyocardial layer in each layer show complicated movements according to expansion and contraction of the heart corresponding to the three-layered structure of the heart including a longitudinal muscle of the endomyocardial layer, a circular muscle of the midmyocardial layer, and a longitudinal muscle of the epimyocardial layer is expressed. Undoubtedly, this phenomenon cannot be checked by a three-dimensional strain gauge image using a strain gauge which does not have a gauge midpoint, for example, and it is information provided for the first time by the three-dimensional strain gauge image in the present embodiment.

Moreover, in the case of ischemic heart disease, it is known that the endomyocardial layer side of the myocardium is first injured due to its sensitiveness. Therefore, it can be said that when local myocardial ischemia is caused by stress echo, it is very useful to compare and observe before and after of the stress using a three-dimensional strain gauge image including a strain gauge in which a gauge midpoint is set. According to such observation, it is expected that for example, when the endomyocardial layer side is injured after the stress to thereby change to a different motion state from that before the stress, the three-dimensional state can be understood clearly and intuitively as a change of a bending state of the line plot with angulation of the strain gauge display of the invention. Moreover, not only for the before and after of the stress but also for progress observation of a change of the wall motion before and after medical care using a drug(eg. dobutamine) and the like, the same effects may be expected.

Figure 17:
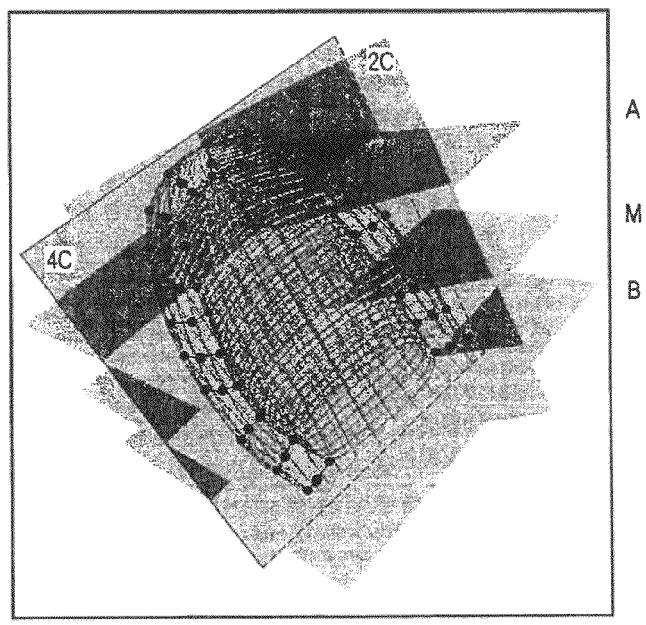
FIG. 17 is a view illustrating another example (apical image) of a three-dimensional strain gauge image including a strain gauge in which a midmyocardial layer gauge point is set.

FIG. 17 is a view illustrating another example (apical image) of a three-dimensional strain gauge image including a strain gauge in which a gauge midpoint is set. As shown in FIG. 17, in the case of an apical image, a difference of moving distance (displacement) between respective layers of endomyocardial and epimyocardial layers according to the shortening movement in the long axis direction is intuitively expressed by strain gauge display rather than the rotation component between the endomyocardial and epimyocardial layers. Accordingly, an effect that which one of the endomyocardial and epimyocardial layers contributes to an increase in wall thickness is easily checked can be expected, for example.

Furthermore, in the present embodiment, for the clinical purpose, one gauge endpoint is set on the endomyocardial layer, another gauge endpoint is set on the epimyocardial layer, and a gauge midpoint is set at a middle point between gauge endpoints in a time phase of end-diastole in order to observe the motion of each of the endomyocardial layer, midmyocardial layer, and epimyocardial layer of the myocardium. However, the invention is not limited thereto, and there is no limitation in positions of gauge endpoint and gauge midpoint as long as they are effective in visually showing local deformation of the myocardium. Moreover, in the present embodiment, one gauge midpoint is set between gauge endpoints in order to observe the motion of each of the endomyocardial layer, midmyocardial layer, and epimyocardial layer of the myocardium. However, the invention is not limited to this example, and a desired number of gauge midpoints may be set at desired positions as long as they are located between gauge endpoints. In this manner, a strain gauge configured to include a plurality of line segments can be defined by setting at least one midpoint.

(Fifth Embodiment)

Next, a fifth embodiment of the invention will be described. An ultrasonic diagnostic apparatus according to the present embodiment calculates quantification information on a displacement component or rotation difference of endomyocardial and epimyocardial layers of the heart or quantification information on a displacement component or rotation difference of the endomyocardial and epimyocardial layers with respect to the midmyocardial layer (hereinafter, both information are referred to as 'rotation difference information') using a result of three-dimensional speckle tracking processing and displays the information in a predetermined form independently or together with a three-dimensional strain gauge image. Moreover, in the present embodiment, it is preferable that a predetermined short-axis level (for example, A plane, M plane, or B plane) be set beforehand.

Figure 18:
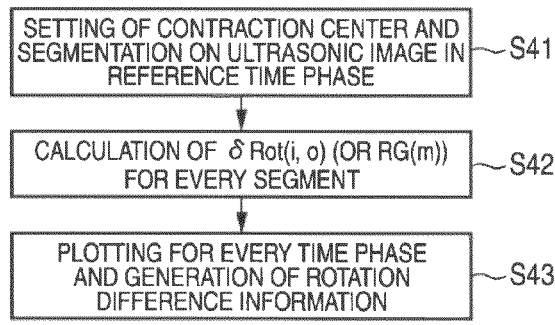
FIG. 18 is a flow chart illustrating the flow of rotation difference information generation processing.

FIG. 18 is a flow chart illustrating the flow of rotation difference information generation processing. This rotation difference information generation processing is executed, for example, before and after generation of a three-dimensional strain gauge image or in parallel with generation of the three-dimensional strain gauge image by the motion information calculating unit 37.

First, the rotation difference information generating unit 37 sets the systolic center for an ultrasonic image in each time phase and calculates rotation difference information for every anatomical segment regarding a myocardial portion (step S41). In setting the systolic center, for example, the position of the center of gravity of an endomyocardial layer is adopted. Moreover, allocation (segmentation) of the anatomical segment may be executed, for example, by assigning a section, which is specified beforehand at the time of data collection, as a display format and making the user adjusting the probe position according to the display format. By this segmentation, the myocardium is divided into anatomical regions of Sept/Ant/Lat/Post/Inf, for example.

Then, the rotation difference information generating unit 37 calculates rotation information in each region of the myocardium in each time phase according to the following Expression (1), for example, in the unit of 'degree' on the condition that a direction in which the positions of endomyocardial and epimyocardial layers rotate counterclockwise for the position of the center of gravity of the endomyocardial layer in time phase of end-diastole is positive and a direction in which they rotate clockwise is negative (step S42).

$$\delta Rot(i, o) = Rot(i) - Rot(o) \quad \text{(Expression 1)}$$

In addition, $\delta Rot(i, o)$ means a difference value of relative rotation of an epimyocardial layer with respect to an endomyocardial layer, $Rot(i)$ means a rotation angle of the endomyocardial layer in each region, and $Rot(o)$ means a rotation angle of the epimyocardial layer in each region.

Figure 19:
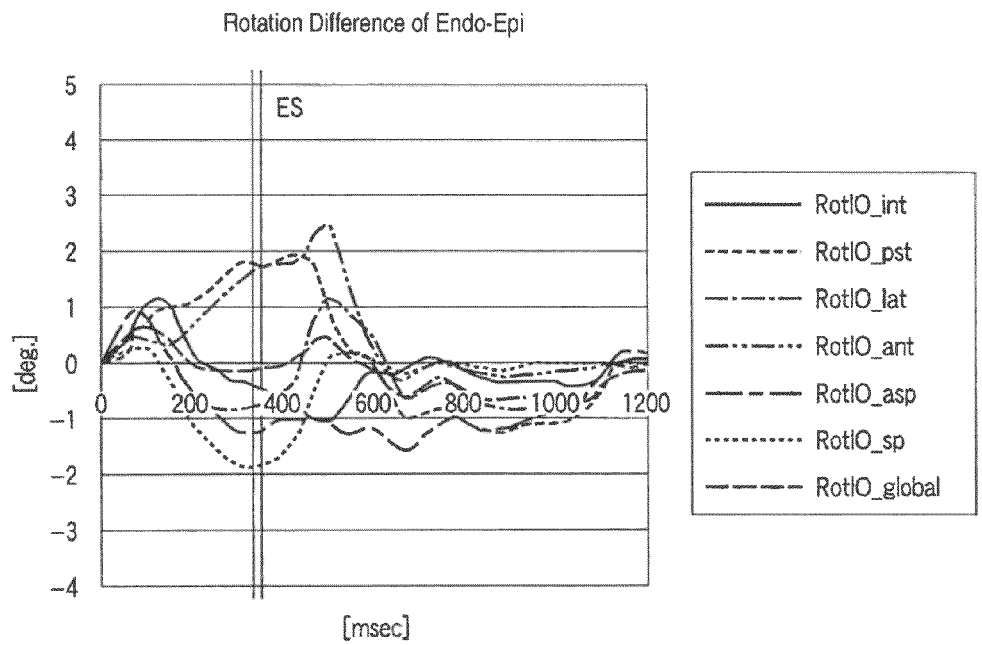
FIG. 19 is a view illustrating an example of rotation difference information.

Then, the rotation difference information generating unit 37 generates, for example, rotation difference information shown in FIG. 19 by plotting rotation information for every region of the myocardium in each time phase (step S43). The generated rotation difference information is displayed in steps S4, S15, and S25, for example. In FIG. 19, 'ES' indicates a time phase of end-systole and 'global' indicates an average value in the entire myocardium. The generated rotation difference information is displayed in steps S4, S15, and S25, for example.

In the above example, an example using the Expression (1) for calculating rotation difference information from only information on endomyocardial and epimyocardial layers is shown. However, the invention is not limited to the example. For example, the rotation difference information may be calculated according to the following Expression (2) in which the motion of the midmyocardial layer is also taken into consideration.

That is, rotation information RG(m) which is a relative rotation difference between a midmyocardial layer and an epimyocardial layer with respect to a rotation difference between an endomyocardial layer and the midmyocardial layer is calculated for each region of the myocardium in each time phase according to the following Expression (2), in the unit of 'degree' on the condition that a direction in which the positions of endomyocardial and epimyocardial layers and midmyocardial layer rotate counterclockwise for the position of the center of gravity of the endomyocardial layer in time phase of end-diastole is positive and a direction in which they rotate clockwise is negative (step S42).

$$\begin{aligned} RG(m) &= \delta Rot(i, m) - \delta Rot(m, o) \quad \text{(Expression 2)} \\ &= Rot(i) - Rot(m) - (Rot(m) - Rot(o)) \\ &= Rot(i) - 2 * Rot(m) + Rot(o) \end{aligned}$$

In addition, $Rot(i)$ is a rotation angle of the endomyocardial layer in each region, $Rot(o)$ is a rotation angle of the epimyocardial layer in each region, and $Rot(m)$ means a rotation angle of the midmyocardial layer in each region.

Figure 20:
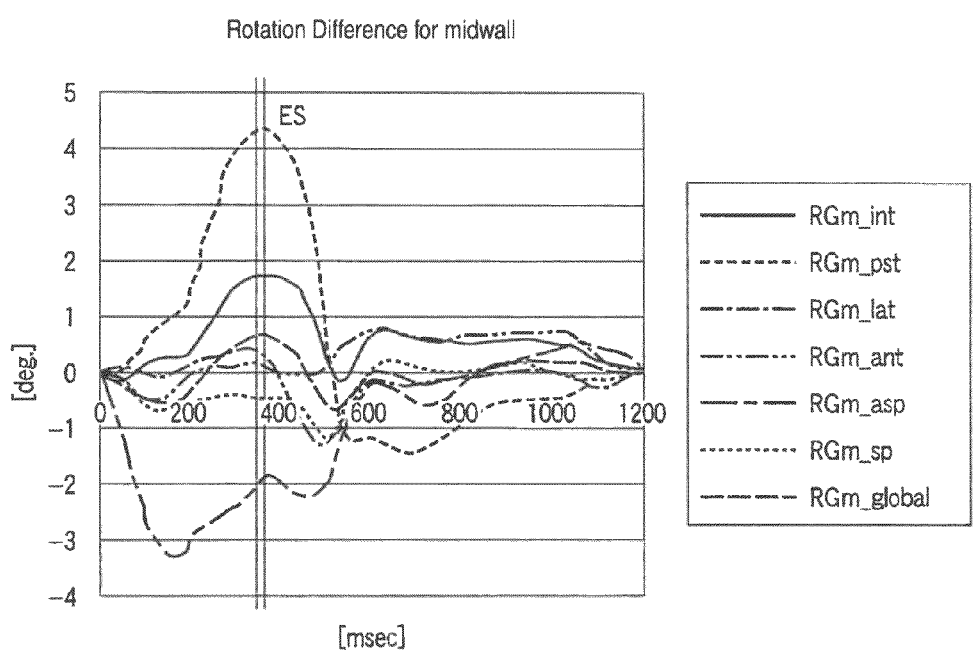
FIG. 20 is a view illustrating an example of rotation difference information.

In this case, the rotation difference information generating unit 37 generates, for example, inside and outside rotation difference information shown in FIG. 20 by plotting rotation information for every region of the myocardium in each time phase (step S43). Similarly in FIG. 20, 'ES' indicates a time phase of end-systole and 'global' indicates an average value in the entire myocardium. The generated rotation difference information is displayed in steps S4, S15, and S25, for example.

In this way, a rotation difference between endomyocardial and epimyocardial layers in each region of the myocardium or a rotation difference of the endomyocardial and epimyocardial layers sides with respect to the midmyocardial layer is expressed quantitatively. By displaying it in a graph, it may be possible to analyze a temporal change in the rotation difference between endomyocardial and epimyocardial layers in each region of the myocardium or the rotation difference of the endomyocardial and epimyocardial layers sides with respect to the midmyocardial layer. Moreover, parametric imaging which shows new wall motion information becomes possible by converting the obtained rotation difference parameter into a color code and displaying it on the MPR image so as to superimpose by matching the positions. As another method of the parametric imaging, it is possible to convert a rotation difference parameter into a color code, to perform mapping to the position on the endomyocardial layer surface, and to display it in a three-dimensional manner by rendering processing. Furthermore, it can be said to be a suitable application to support recognition of a state of a temporal change of the wall motion, for a temporal change in calculation parameter in the present embodiment, particularly by graphical display of a result of a change obtained by using processing including a difference or by displaying the result of the change by parametric imaging.

In addition, the invention is not limited to the embodiments described above and may be embodied in practice by modifying constituent components without departing from the scope and spirit of the invention. For example, specific modifications include the following examples.

(1) Each of the functions in the present embodiments may be realized by installing a program, which is used to execute corresponding processing, in a computer, such as a workstation, and then loading the program into a memory. In this case, a program capable of causing a computer to execute a corresponding technique may be distributed in a state where the program is stored in recording media, such as a magnetic disk (for example, a floppy disk or a hard disk), an optical disk (for example, a CD-ROM or a DVD), and a semiconductor memory.

(2) The display form of a three-dimensional strain gauge image described in each of the embodiments is merely an example, and the technical idea of the invention is not limited thereto. The display form may be modified in various ways. For example, three-dimensional strain gauge images collected at different time may be displayed simultaneously. Such a display form is especially effective for observation of temporal change of a diagnostic portion, such as postoperative observation.

In addition, various kinds of inventions may be realized by proper combination of the plurality of constituent components disclosed in the embodiments described above. For example, some constituent components may be eliminated from all components shown in the above embodiments. Moreover, the constituent components in different embodiments may be appropriately combined.

What is claimed is:

1. An ultrasonic diagnostic apparatus, comprising:
an ultrasonic scanner that collects volume data over one or more periods of movement of tissue of a subject body, which moves periodically, by ultrasonically scanning the tissue of the subject body;
interest region setting circuitry configured to set a three-dimensional region of interest of the tissue of the subject body for the volume data at a predetermined time;
motion vector information generating circuitry configured to generate three-dimensional motion vector information on the region of interest at times other than the predetermined time by processing using pattern matching;
gauge setting circuitry configured to set a reference surface in a three-dimensional space at the predetermined time, set at least one three-dimensional position of a strain gauge on the reference surface, and set the at least one three-dimensional position of the strain gauge at times other than the predetermined time, using the three-dimensional motion vector information on the region of interest, the strain gauge being a line segment on the tissue of the subject body and extending in a wall thickness direction of heart tissue;
image generating circuitry configured to generate a three-dimensional strain gauge image depicting the at least one three-dimensional position of the strain gauge and the position of the reference surface in the three-dimensional space in a three-dimensional manner; and
a display that displays the three-dimensional strain gauge image.

2. The ultrasonic diagnostic apparatus according to claim 1,
wherein the gauge setting circuitry sets the strain gauge as a plurality of line segments connecting two endpoints and one or more middle points, which exist between the endpoints, with each other.

3. The ultrasonic diagnostic apparatus according to claim 1, further comprising:
setting circuitry configured to set a short-axis position of the heart and a rotation center when the short-axis position is set as a reference position on volume data in a plurality of time phases including the predetermined time phase,
calculation circuitry configured to calculate rotation angles of positions of endomyocardial and epimyocardial layers from a reference time when the rotation center is set as a reference, and
rotation difference information circuitry configured to generate first rotation difference information indicating a difference between the rotation angle of the endomyocardial layer position and the rotation angle of the epimyocardial layer position, and
the display displays the first rotation difference information.

4. The ultrasonic diagnostic apparatus according to claim 3,
wherein the calculation circuitry calculates a rotation angle of a midmyocardial layer position, which exists between the endomyocardial layer position and the epimyocardial layer position, from the reference time,
the rotation difference information generating circuitry generates second rotation difference information indicating a difference between the rotation angle of the endomyocardial layer position and the rotation angle of the midmyocardial layer position and third rotation difference information indicating a difference between the rotation angle of the epimyocardial layer position and the rotation angle of the midmyocardial layer position, and
the display displays the second rotation difference information and the third rotation difference information.

5. The ultrasonic diagnostic apparatus according to claim 4,
wherein the image generating circuitry generates the three-dimensional strain gauge image obtained by converting at least one of the first rotation difference information, the second rotation difference information, and the third rotation difference information into color information and mapping the converted color information to a corresponding position.

6. The ultrasonic diagnostic apparatus according to claim 3,
wherein the rotation difference information generating circuitry generates the rotation difference information for every anatomical segment regarding a myocardial portion of the heart, and
the display displays the rotation difference information for every anatomical segment as a temporal change curve.

7. The ultrasonic diagnostic apparatus according to claim 3,
wherein the rotation difference information generating circuitry generates information on a temporal change of the rotation difference information by performing subtraction of the rotation difference information corresponding to volume data collected at a different time, and
the display displays the information on the temporal change of the rotation difference information.

8. The ultrasonic diagnostic apparatus according to claim 1,
wherein the display simultaneously displays the plurality of three-dimensional strain gauge images corresponding to volume data collected at a different time.

9. The ultrasonic diagnostic apparatus according to claim 1, wherein the display is configured to display a strain gauge set in a predetermined cross section from among a plurality of strain gauges set in a region of interest of a myocardium.

10. The ultrasonic diagnostic apparatus according to claim 9, wherein the predetermined cross section is a cross section orthogonal to a long-axis.

11. The ultrasonic diagnostic apparatus according to claim 1, wherein the image generating circuitry is configured to calculate a regression plane on an MPR image and to generate the three-dimensional strain gauge image by projecting the strain gauge to the regression plane.

12. The ultrasonic diagnostic apparatus of claim 1, further comprising:
a processor configured to perform, using the volume data, segmentation on a myocardial region.

13. An ultrasonic diagnostic apparatus, comprising:
an ultrasonic scanner that collects volume data over one or more periods of movement of tissue of a subject body, which moves periodically, by ultrasonically scanning the tissue of the subject body;
interest region setting circuitry configured to set a three-dimensional region of interest of the tissue of the subject body for the volume data at a predetermined time;
motion vector information generating circuitry configured to generate three-dimensional motion vector information on the region of interest at times other than the predetermined time by processing using pattern matching;
gauge setting circuitry configured to set a reference surface in a three-dimensional space at the predetermined time, set at least one three-dimensional position of a strain gauge on the reference surface, and set the at least one three-dimensional position of the strain gauge at times other than the predetermined time, using the three-dimensional motion vector information on the region of interest, the strain gauge being a line segment on the tissue of the subject body and extending in a wall thickness direction of heart tissue;

section circuitry configured to set at least one arbitrary section for volume data at each time;

image generating circuitry configured to generate a three-dimensional strain gauge image obtained by projection of the strain gauge disposed in the three-dimensional space onto at least the one arbitrary section, the three-dimensional strain gauge image depicting the at least one three-dimensional position of the strain gauge and the position of the reference surface; and a display that displays the three-dimensional strain gauge image.

14. The ultrasonic diagnostic apparatus according to claim 13, further comprising:
a processor configured to set an multi-planar reconstruction (MPR) image dynamically on at least the one arbitrary section so as to follow the movement of a tissue portion including an multi-planar reconstruction (MPR) image.

15. The ultrasonic diagnostic apparatus according to claim 13,
wherein the gauge setting circuitry sets the strain gauge as a plurality of line segments connecting two endpoints and one or more middle points, which exist between the endpoints, with each other.

16. The ultrasonic diagnostic apparatus according to claim 13, further comprising:
setting circuitry configured to set a short-axis position of the heart and a systolic center when the short-axis position is set as a reference position on volume data in a plurality of time phases including the predetermined time phase,
calculation circuitry configured to calculate rotation angles of positions of endomyocardial and epimyocardial layers from a reference time when the rotation center is set as a reference, and
rotation difference information generating circuitry configured to generate first rotation difference information indicating a difference between the rotation angle of the endomyocardial layer position and the rotation angle of the epimyocardial layer position, and
the display displays the first rotation difference information.

17. The ultrasonic diagnostic apparatus according to claim 16,
wherein the calculation circuitry calculates a rotation angle of a midmyocardial layer position, which exists between the endomyocardial layer position and the epimyocardial layer position, from the reference time,
the rotation difference information generating circuitry generates second rotation difference information indicating a difference between the rotation angle of the endomyocardial layer position and the rotation angle of the midmyocardial layer position and third rotation difference information indicating a difference between the rotation angle of the epimyocardial layer position and the rotation angle of the midmyocardial layer position, and
the display displays the second rotation difference information and the third rotation difference information.

18. The ultrasonic diagnostic apparatus according to claim 17,
wherein the image generating circuitry generates the three-dimensional strain gauge image obtained by converting at least one of the first rotation difference information, the second rotation difference information, and the third rotation difference information into color information and mapping the converted color information to a corresponding position.

19. The ultrasonic diagnostic apparatus according to claim 16,
wherein the rotation difference information generating circuitry generates the rotation difference information for every anatomical segment regarding a myocardial portion of the heart, and
the display displays the rotation difference information for every anatomical segment as a temporal change curve.

20. The ultrasonic diagnostic apparatus according to claim 16,
wherein the rotation difference information generating circuitry generates information on a temporal change of the rotation difference information by performing subtraction of the rotation difference information corresponding to volume data collected at a different time, and
the display displays the information on the temporal change of the rotation difference information.

21. The ultrasonic diagnostic apparatus according to claim 13,
wherein the display simultaneously displays the plurality of three-dimensional strain gauge images corresponding to volume data collected at a different time.

22. An ultrasonic diagnostic apparatus, comprising:
an ultrasonic scanner that collects volume data over one or more periods of movement of tissue of a subject body, which moves periodically, by ultrasonically scanning the tissue of the subject body;
section setting circuitry configured to set at least one arbitrary section for volume data at each time;
interest region setting circuitry configured to set a region of interest of the tissue of the subject body on at least the one arbitrary section at a predetermined time;
motion vector information generating circuitry configured to generate three-dimensional motion vector information on the region of interest in time phases other than the predetermined time phase by processing using pattern matching;
gauge setting circuitry configured to set a reference surface in a three-dimensional space at the predetermined time, set at least one three-dimensional position of a strain gauge on the reference surface, and set the at least one three-dimensional position of the strain gauge at times other than the predetermined time, using the three-dimensional motion vector information on the region of interest, the strain gauge being a line segment on the tissue of the subject body and extending in a wall thickness direction of heart tissue;
image generating circuitry configured to generate a three-dimensional strain gauge image in which the strain gauge disposed in the three-dimensional space is set at a corresponding position on at least the one arbitrary section, the three-dimensional strain gauge image depicting the at least one three-dimensional position of the strain gauge and the position of the reference surface; and
a display that displays the three-dimensional strain gauge image.

23. The ultrasonic diagnostic apparatus according to claim 22, further comprising:
a processor configured to set an multi-planar reconstruction (MPR) image dynamically on at least the one arbitrary section so as to follow the movement of a tissue portion including an multi-planar reconstruction (MPR) image.

24. The ultrasonic diagnostic apparatus according to claim 22,
wherein the gauge setting circuitry sets the strain gauge as a plurality of line segments connecting two endpoints and one or more middle points, which exist between the endpoints, with each other.

25. The ultrasonic diagnostic apparatus according to claim 22, further comprising:
setting circuitry configured to set a short-axis position of the heart and a systolic center when the short-axis position is set as a reference position on volume data at a plurality of times including the predetermined time,
calculation circuitry configured to calculate rotation angles of positions of endomyocardial and epimyocardial layers from a reference time when the rotation center is set as a reference, and
rotation difference information generating circuitry configured to generate first rotation difference information indicating a difference between the rotation angle of the endomyocardial layer position and the rotation angle of the epimyocardial layer position, and
the display displays the first rotation difference information.

26. The ultrasonic diagnostic apparatus according to claim 25,
wherein the calculation circuitry calculates a rotation angle of a midmyocardial layer position, which exists between the endomyocardial layer position and the epimyocardial layer position, from the reference time,
the rotation difference information generating circuitry generates second rotation difference information indicating a difference between the rotation angle of the endomyocardial layer position and the rotation angle of the midmyocardial layer position and third rotation difference information indicating a difference between the rotation angle of the epimyocardial layer position and the rotation angle of the midmyocardial layer position, and
the display displays the second rotation difference information and the third rotation difference information.

27. The ultrasonic diagnostic apparatus according to claim 26,
wherein the image generating circuitry generates the three-dimensional strain gauge image obtained by converting at least one of the first rotation difference information, the second rotation difference information, and the third rotation difference information into color information and mapping the converted color information to a corresponding position.

28. The ultrasonic diagnostic apparatus according to claim 25,
wherein the rotation difference information generating circuitry generates the rotation difference information for every anatomical segment regarding a myocardial portion of the heart, and
the display displays the rotation difference information for every anatomical segment as a temporal change curve.

29. The ultrasonic diagnostic apparatus according to claim 25,
wherein the rotation difference information generating circuitry generates information on a temporal change of the rotation difference information by performing subtraction of the rotation difference information corresponding to volume data collected at a different time, and
the display displays the information on the temporal change of the rotation difference information.

30. The ultrasonic diagnostic apparatus according to claim 22,
wherein the display simultaneously displays the plurality of three-dimensional strain gauge images corresponding to volume data collected at a different time.

31. An ultrasonic image processing apparatus, comprising:
an ultrasonic scanner that collects volume data collected over one or more periods of movement of tissue of a subject body, which moves periodically, by ultrasonically scanning the tissue of the subject body;
interest region setting circuitry configured to set a three-dimensional region of interest of the tissue of the subject body for the volume data at a predetermined time;
motion vector information generating circuitry configured to generate three-dimensional motion vector information on the region of interest at times other than the predetermined time by processing using pattern matching;
gauge setting circuitry configured to set a reference surface in a three-dimensional space at the predetermined time, set at least one three-dimensional position of a strain gauge on the reference surface, and set the at least one three-dimensional position of the strain gauge at times other than the predetermined time, using the three-dimensional motion vector information on the region of interest, the strain gauge being a line segment on the tissue of the subject body and extending in a wall thickness direction of heart tissue;
image generating circuitry configured to generate a three-dimensional strain gauge image depicting the at least one three-dimensional position of the strain gauge and the position of the reference surface in the three-dimensional space in a three-dimensional manner; and
a display that displays the three-dimensional strain gauge image.

32. An ultrasonic image processing apparatus, comprising:
an ultrasonic scanner that collects volume data collected over one or more periods of movement of tissue of a subject body, which moves periodically, by ultrasonically scanning the tissue of the subject body;
interest region setting circuitry configured to set a three-dimensional region of interest of the tissue of the subject body for the volume data at a predetermined time;
motion vector information generating circuitry configured to generate three-dimensional motion vector information on the region of interest at times other than the predetermined time by processing using pattern matching;
gauge setting circuitry configured to set a reference surface in a three-dimensional space at the predetermined time, set at least one three-dimensional position of a strain gauge on the reference surface, and set the at least one three-dimensional position of the strain gauge at times other than the predetermined time, using the three-dimensional motion vector information on the region of interest, the strain gauge being a line segment on the tissue of the subject body and extending in a wall thickness direction of heart tissue;

section setting circuitry configured to set at least one arbitrary section for volume data at each time;
image generating circuitry configured to generate a three-dimensional strain gauge image obtained by projection of the strain gauge disposed in the three-dimensional space onto at least the one arbitrary section, the three-dimensional strain gauge image depicting the at least one three-dimensional position of the strain gauge and the position of the reference surface; and
a display that displays the three-dimensional strain gauge image.

33. An ultrasonic image processing apparatus, comprising:
an ultrasonic scanner configured to collect volume data collected over one or more periods of movement of tissue of a subject body, which moves periodically, by ultrasonically scanning the tissue of the subject body;
section setting circuitry configured to set at least one arbitrary section for volume data at each time;
interest region setting circuitry configured to set a region of interest of the tissue of the subject body on at least the one arbitrary section at a predetermined time;
motion vector information generating circuitry configured to generate three-dimensional motion vector information on the region of interest at times other than the predetermined time by processing using pattern matching;
gauge setting circuitry configured to set a reference surface in a three-dimensional space at the predetermined time, set at least one three-dimensional position of a strain gauge on the reference surface, using the three-dimensional motion vector information on the region of interest, the strain gauge being a line segment on the tissue of the subject body and extending in a wall thickness direction of heart tissue;
image generating circuitry configured to generate a three-dimensional strain gauge image in which the strain gauge disposed in the three-dimensional space is set at a corresponding position on at least the one arbitrary section, the three-dimensional strain gauge image depicting the at least one three-dimensional position of the strain gauge and the position of the reference surface; and
a display that displays the three-dimensional strain gauge image.

34. A medical image processing apparatus, comprising:
an ultrasonic scanner that collects volume data collected for tissue of a subject body, which moves periodically, over one or more periods, by ultrasonically scanning the tissue of the subject body;
interest region setting circuitry configured to set a three-dimensional region of interest of the tissue of the subject body for the volume data at a predetermined time;
motion vector information generating circuitry configured to generate three-dimensional motion vector information on the region of interest at times other than the predetermined time by processing using pattern matching;
gauge setting circuitry configured to set a reference surface in a three-dimensional space at the predetermined time, set at least one three-dimensional position of a strain gauge on the reference surface, using the three-dimensional motion vector information on the region of interest, the strain gauge being a line segment on the tissue of the subject body and extending in a wall thickness direction of heart tissue;
image generating circuitry configured to generate a three-dimensional strain gauge image depicting the at least one three-dimensional position of the strain gauge and the position of the reference surface in the three-dimensional space in a three-dimensional manner; and
a display that displays the three-dimensional strain gauge image.

35. A medical image processing apparatus, comprising:
an ultrasonic scanner configured to collect volume data collected for tissue of a subject body, which moves periodically, over one or more periods, by ultrasonically scanning the tissue of the subject body;
interest region setting circuitry configured to set a three-dimensional region of interest of the tissue of the subject body for the volume data at a predetermined time;
motion vector information generating circuitry configured to generate three-dimensional motion vector information on the region of interest at times other than the predetermined time by processing using pattern matching;
gauge setting circuitry configured to set a reference surface in a three-dimensional space at the predetermined time, set at least one three-dimensional position of a strain gauge on the reference surface, using the three-dimensional motion vector information on the region of interest, the strain gauge being a line segment on the tissue of the subject body and extending in a wall thickness direction of heart tissue;
section setting circuitry configured to set at least one arbitrary section for volume data at each time;
image generating circuitry configured to generate a three-dimensional strain gauge image obtained by projection of the strain gauge disposed in the three-dimensional space onto at least the one arbitrary section, the three-dimensional strain gauge image depicting the at least one three-dimensional position of the strain gauge and the position of the reference surface; and
a display that displays the three-dimensional strain gauge image.

36. A medical image processing apparatus, comprising:
an ultrasonic scanner configured to collect volume data collected for tissue of a subject body, which moves periodically, over one or more periods, by ultrasonically scanning the tissue of the subject body;
section setting circuitry configured to set at least one arbitrary section for volume data in each time phase;
interest region setting circuitry configured to set a region of interest of the tissue of the subject body on at least the one arbitrary section at a predetermined time;
motion vector information generating circuitry configured to generate three-dimensional motion vector information on the region of interest at times other than the predetermined time by processing using pattern matching;
gauge setting circuitry configured to set a reference surface in a three-dimensional space at the predetermined time, set at least one three-dimensional position of a strain gauge on the reference surface, using the three-dimensional motion vector information on the region of interest, the strain gauge being a line segment on the tissue of the subject body and extending in a wall thickness direction of heart tissue;
image generating circuitry configured to generate a three-dimensional strain gauge image in which the strain gauge disposed in the three-dimensional space is set at a corresponding position on at least the one arbitrary section, the three-dimensional strain gauge image depicting the at least one three-dimensional position of the strain gauge and the position of the reference surface; and
a display that displays the three-dimensional strain gauge image.

* * * * *